United States Patent
Petroff et al.

(10) Patent No.: US 12,193,789 B2
(45) Date of Patent: Jan. 14, 2025

(54) OPTICAL COHERENCE TOMOGRAPHY AND PRESSURE BASED SYSTEMS AND METHODS

(71) Applicant: LightLab Imaging, Inc., Westford, MA (US)

(72) Inventors: Christopher Petroff, Groton, MA (US); Joseph M. Schmitt, Andover, MA (US)

(73) Assignee: LightLab Imaging, Inc., Westford, MA (US)

(*) Notice: Subject to any disclaimer, the term of this patent is extended or adjusted under 35 U.S.C. 154(b) by 902 days.

(21) Appl. No.: 16/937,117

(22) Filed: Jul. 23, 2020

(65) Prior Publication Data

US 2020/0352446 A1 Nov. 12, 2020

Related U.S. Application Data

(63) Continuation of application No. 14/122,574, filed as application No. PCT/US2012/037717 on May 14, 2012, now abandoned.

(Continued)

(51) Int. Cl.
*A61B 5/00* (2006.01)
*A61B 1/015* (2006.01)
(Continued)

(52) U.S. Cl.
CPC ............ *A61B 5/0084* (2013.01); *A61B 1/015* (2013.01); *A61B 1/07* (2013.01); *A61B 5/0066* (2013.01);
(Continued)

(58) Field of Classification Search
CPC ... A61B 5/0084; A61B 5/0215; A61B 5/6876; A61B 5/7282; A61B 5/7278;
(Continued)

(56) References Cited

U.S. PATENT DOCUMENTS 2,050,630 A 8/1936 Reid
2,773,369 A 12/1956 Kiemm
(Continued)

FOREIGN PATENT DOCUMENTS

CN 101869472 A 10/2010
EP 0445918 A1 9/1991
(Continued)

OTHER PUBLICATIONS

Patent Examination report No. 1 mailed from IP Australia on Dec. 16, 2015 for Australian Application No. 2012262883 (3 pages).

(Continued)

*Primary Examiner* — Joseph M Santos Rodriguez
*Assistant Examiner* — Amy Shafqat
(74) *Attorney, Agent, or Firm* — Lerner David LLP

(57) ABSTRACT

In part, the invention relates to methods, apparatus, and systems suitable for determining a fractional flow reserve (FFR) and variations of modifications thereof One embodiment relates to a method and apparatus for obtaining a corrected FFR in a vessel having a stenosis. In one aspect, the invention relates to an apparatus for measuring corrected FFR of a vessel having a stenosis. In one embodiment, the apparatus includes a probe comprising an optical coherence tomography assembly and a pressure assembly; and a processor in communication with the optical coherence tomography assembly and the pressure assembly. In one embodiment, the pressure assembly measures values of pressure in predetermined locations the vessel and communicates them to the processor. In one embodiment, a dual guidewire is used to reduce the interference in the pressure measurement.

20 Claims, 21 Drawing Sheets

Related U.S. Application Data

(60) Provisional application No. 61/529,594, filed on Aug. 31, 2011, provisional application No. 61/490,925, filed on May 27, 2011.

(51) Int. Cl.
| | |
|---|---|
| *A61B 1/07* | (2006.01) |
| *A61B 5/02* | (2006.01) |
| *A61B 5/0215* | (2006.01) |
| *A61B 5/026* | (2006.01) |
| *A61B 5/107* | (2006.01) |

(52) U.S. Cl.
CPC ........ *A61B 5/02028* (2013.01); *A61B 5/0215* (2013.01); *A61B 5/02158* (2013.01); *A61B 5/026* (2013.01); *A61B 5/6876* (2013.01); *A61B 5/7278* (2013.01); *A61B 5/7282* (2013.01); *A61B 5/1076* (2013.01); *A61B 5/1077* (2013.01); *A61B 5/6852* (2013.01); *A61B 2562/0233* (2013.01); *A61B 2562/0247* (2013.01); *A61B 2576/023* (2013.01)

(58) Field of Classification Search
CPC . A61B 5/026; A61B 5/02158; A61B 5/02028; A61B 1/07; A61B 1/015; A61B 5/0066; A61B 2562/0233; A61B 2562/0247; A61B 5/1077; A61B 5/6852; A61B 5/1076; A61B 2576/023
See application file for complete search history.

(56) References Cited

U.S. PATENT DOCUMENTS

| | | | |
|---|---|---|---|
| 3,306,291 A | 2/1967 | Burke | |
| 3,834,372 A | 9/1974 | Turney | |
| 4,434,904 A | 3/1984 | D'Amico et al. | |
| 4,669,999 A | 6/1987 | Miller | |
| 4,971,267 A | 11/1990 | Fulton et al. | |
| 5,185,004 A | 2/1993 | Lashinski | |
| 5,228,441 A | 7/1993 | Lundquist | |
| 5,321,501 A | 6/1994 | Swanson et al. | |
| 5,368,480 A | 11/1994 | Balfour et al. | |
| 5,459,570 A | 10/1995 | Swanson et al. | |
| 5,465,147 A | 11/1995 | Swanson | |
| 5,509,093 A | 4/1996 | Miller et al. | |
| 5,596,996 A | 1/1997 | Johanson et al. | |
| 5,619,368 A | 4/1997 | Swanson | |
| 5,748,598 A | 5/1998 | Swanson et al. | |
| 5,784,352 A | 7/1998 | Swanson et al. | |
| 5,913,437 A | 6/1999 | Ma | |
| 6,111,645 A | 8/2000 | Tearney et al. | |
| 6,134,003 A | 10/2000 | Tearney et al. | |
| 6,160,826 A | 12/2000 | Swanson et al. | |
| 6,191,862 B1 | 2/2001 | Swanson et al. | |
| 6,282,011 B1 | 8/2001 | Tearney et al. | |
| 6,421,164 B2 | 7/2002 | Tearney et al. | |
| 6,445,939 B1 | 9/2002 | Swanson et al. | |
| 6,485,413 B1 | 11/2002 | Boppart et al. | |
| 6,488,637 B1 | 12/2002 | Eder et al. | |
| 6,501,551 B1 | 12/2002 | Tearney et al. | |
| 6,552,796 B2 | 4/2003 | Magnin et al. | |
| 6,564,087 B1 | 5/2003 | Pitris et al. | |
| 6,570,659 B2 | 5/2003 | Schmitt | |
| 6,582,368 B2 | 6/2003 | Holdaway et al. | |
| 6,706,004 B2 | 3/2004 | Tearney et al. | |
| 6,758,818 B2 | 7/2004 | Pantages et al. | |
| 6,879,851 B2 | 4/2005 | McNamara et al. | |
| 6,891,984 B2 | 5/2005 | Petersen et al. | |
| 7,066,819 B2 | 6/2006 | Jeda et al. | |
| 7,121,947 B2 | 10/2006 | Jeda et al. | |
| 7,208,333 B2 | 4/2007 | Flanders et al. | |
| 7,231,243 B2 | 6/2007 | Tearney et al. | |
| 7,241,286 B2 | 7/2007 | Atlas | |
| 7,311,625 B2 | 12/2007 | Nosaka et al. | |
| 7,407,440 B2 | 8/2008 | White | |
| 7,414,779 B2 | 8/2008 | Huber et al. | |
| 7,415,049 B2 | 8/2008 | Flanders et al. | |
| 7,625,366 B2 | 12/2009 | Atlas | |
| 7,715,896 B2 | 5/2010 | Ramzipoor et al. | |
| 7,813,609 B2 | 10/2010 | Petersen et al. | |
| 7,848,791 B2 | 12/2010 | Schmitt et al. | |
| 7,916,387 B2 | 3/2011 | Schmitt | |
| 7,935,060 B2 | 5/2011 | Schmitt et al. | |
| 8,021,366 B2 | 9/2011 | Phan | |
| 8,116,605 B2 | 2/2012 | Petersen et al. | |
| 8,157,741 B2 | 4/2012 | Hirota | |
| 8,206,377 B2 | 6/2012 | Petroff | |
| 8,325,419 B2 | 12/2012 | Schmitt | |
| 8,358,461 B2 | 1/2013 | Huber et al. | |
| 8,412,312 B2 | 4/2013 | Judell et al. | |
| 8,449,468 B2 | 5/2013 | Petersen et al. | |
| 8,478,384 B2 | 7/2013 | Schmitt et al. | |
| 8,478,387 B2 | 7/2013 | Xu | |
| 8,503,844 B2 | 8/2013 | Petersen et al. | |
| 8,581,643 B1 | 11/2013 | Schmitt | |
| 8,582,109 B1 | 11/2013 | Schmitt | |
| 8,582,619 B2 | 11/2013 | Adler | |
| 8,582,934 B2 | 11/2013 | Adler et al. | |
| 8,687,201 B2 | 4/2014 | Adler | |
| 8,786,336 B1 | 7/2014 | Schmitt | |
| 8,831,321 B1 | 9/2014 | Elbasiony | |
| 8,948,228 B2 | 2/2015 | Adler | |
| 8,953,911 B1 | 2/2015 | Xu et al. | |
| 9,259,161 B2 | 2/2016 | Suchecki et al. | |
| 2002/0068853 A1 | 6/2002 | Adler | |
| 2002/0161351 A1 | 10/2002 | Samson et al. | |
| 2003/0045798 A1 | 3/2003 | Hular et al. | |
| 2005/0187422 A1 | 8/2005 | Maschke | |
| 2005/0201662 A1 | 9/2005 | Petersen et al. | |
| 2006/0074318 A1 | 4/2006 | Ahmed et al. | |
| 2006/0095065 A1 | 5/2006 | Tanimura et al. | |
| 2007/0066890 A1 | 3/2007 | Maschke | |
| 2007/0142729 A1 | 6/2007 | Pfeiffer et al. | |
| 2007/0232893 A1 | 10/2007 | Tanioka | |
| 2008/0269572 A1* | 10/2008 | Kanz | A61B 5/0006 600/301 |
| 2009/0018393 A1* | 1/2009 | Dick | A61B 5/0066 600/109 |
| 2009/0174931 A1 | 7/2009 | Huber et al. | |
| 2009/0177094 A1* | 7/2009 | Brown | A61B 5/0066 606/2 |
| 2009/0306520 A1 | 12/2009 | Schmitt et al. | |
| 2010/0076320 A1 | 3/2010 | Petersen et al. | |
| 2011/0066047 A1 | 3/2011 | Belleville et al. | |
| 2011/0071404 A1 | 3/2011 | Schmitt et al. | |
| 2011/0085977 A1* | 4/2011 | Rosenmeier | A61K 51/04 424/9.1 |
| 2011/0101207 A1 | 5/2011 | Schmitt | |
| 2011/0137140 A1* | 6/2011 | Tearney | A61B 5/021 600/310 |
| 2011/0157686 A1 | 6/2011 | Huber et al. | |
| 2011/0201924 A1* | 8/2011 | Tearney | G01N 21/4795 600/425 |
| 2011/0228280 A1 | 9/2011 | Schmitt et al. | |
| 2012/0238869 A1 | 9/2012 | Schmitt et al. | |
| 2012/0250028 A1 | 10/2012 | Schmitt et al. | |
| 2012/0277580 A1 | 11/2012 | Le et al. | |
| 2012/0310081 A1 | 12/2012 | Adler et al. | |
| 2013/0010303 A1 | 1/2013 | Petersen et al. | |
| 2013/0012811 A1 | 1/2013 | Schmitt et al. | |
| 2013/0023761 A1 | 1/2013 | Petroff | |
| 2013/0051728 A1 | 2/2013 | Petroff | |
| 2013/0072805 A1 | 3/2013 | Schmitt et al. | |
| 2013/0131523 A1* | 5/2013 | Suchecki | A61B 5/02158 600/486 |
| 2013/0310698 A1 | 11/2013 | Judell et al. | |
| 2014/0018669 A1 | 1/2014 | Xu | |
| 2014/0024931 A1 | 1/2014 | Winston et al. | |
| 2014/0094697 A1 | 4/2014 | Petroff et al. | |
| 2014/0114182 A1 | 4/2014 | Petersen et al. | |
| 2014/0142427 A1 | 5/2014 | Petroff | |
| 2014/0142432 A1 | 5/2014 | Hutchins et al. | |

(56) References Cited

U.S. PATENT DOCUMENTS

| | | |
|---|---|---|
| 2014/0142436 A1 | 5/2014 | Hutchins et al. |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0268167 A1 | 9/2014 | Friedman et al. |
| 2014/0276011 A1 | 9/2014 | Schmitt et al. |
| 2014/0309536 A1 | 10/2014 | Douk et al. |
| 2014/0379269 A1 | 12/2014 | Schmitt |

FOREIGN PATENT DOCUMENTS

| | | |
|---|---|---|
| EP | 2713858 A1 | 4/2014 |
| JP | S49109942 A | 10/1974 |
| JP | H01172801 U | 12/1989 |
| JP | H7184888 A | 7/1995 |
| JP | H07286920 A | 10/1995 |
| JP | H1033689 A | 2/1998 |
| JP | H1066696 A | 3/1998 |
| JP | 2005501586 A | 1/2005 |
| JP | 2005503203 A | 2/2005 |
| JP | 2005230552 A | 9/2005 |
| JP | 2005291945 A | 10/2005 |
| JP | 2007083054 A | 4/2007 |
| JP | 2007083057 A | 4/2007 |
| JP | 2007167645 A | 7/2007 |
| JP | 2010233883 A | 10/2010 |
| JP | 2010533049 A | 10/2010 |
| JP | 2012533353 A | 12/2012 |
| JP | 2013154192 A | 8/2013 |
| JP | 2014525761 A | 10/2014 |
| WO | 2011008822 A2 | 1/2011 |
| WO | 2011090744 A2 | 7/2011 |
| WO | 2012166332 A1 | 12/2012 |

OTHER PUBLICATIONS

English translation of Offie Action of Japanese Patent Office mailed Jan. 12, 2016 for Japanese Patent Application No. 2014513532 (5 pages).

Examination Report issued by European Patent Office for EP12724450.7 on Apr. 18, 2016 (6 pages).

Mondofacto, Charrie Scale, [online], Mar. 5, 2000 [retrieved Feb. 1, 2012]. Retrieved from the internet URL: http://www.mondofacto.com/facts/dictionary?Charriere+scale.

Search Report by Registered Search Organization for Japanese Patent Application No. 2014513532 dated Dec. 18, 2015; 8 pages.

Search Report by Registered Search Organization for Japanese Application No. 2018219171 dated Aug. 29, 2019; 21 pages.

* cited by examiner

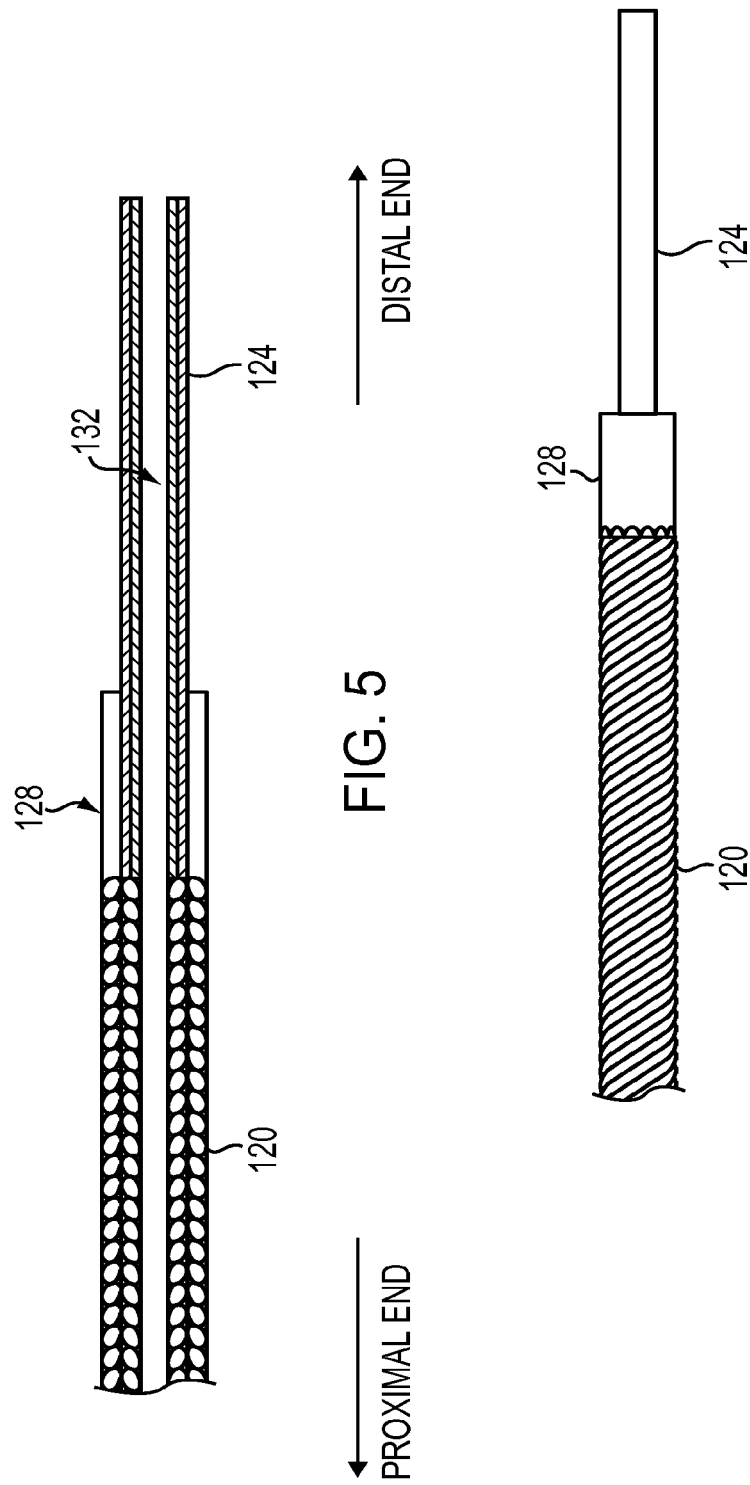

OPTICAL COHERENCE TOMOGRAPHY AND PRESSURE BASED SYSTEMS AND METHODS

CROSS-REFERENCE TO RELATED APPLICATIONS

This present application is a continuation of U.S. application Ser. No. 14/122,574, which is a national phase entry under 35 U.S.C. § 371 of International Application No. PCT/US2012/037717 filed May 14, 2012, which claims priority from U.S. Provisional Application No. 61/529,594 filed Aug. 31, 2011 and U.S. Provisional Application No. 61/490,925 filed May 27, 2011, each of which are herein incorporated by reference in their entireties.

FIELD OF THE INVENTION

In part, the invention relates generally to the field of catheters and medical diagnostics and more specifically to the field of intra-lumen pressure measurement and imaging devices.

BACKGROUND OF THE INVENTION

Treating vessels with stenotic lesions and other full or partial blockages present many challenges to a clinician. Determining the amount of flow through a narrowed or stenotic region of a blood vessel helps a clinician evaluate the severity of the obstruction and select a treatment. Pressure wires inserted into the vessel at locations before and after the stenosis detect pressure values that can be used to ascertain blood flow through the artery. The values can be used to inform a treatment regimen.

Typically, to make diagnostic decisions based on pressure readings, adenosine is administered to the patient and pressure readings are taken first at the ostium or initial opening of the vessel and then distal to the stenotic lesion. The pressure measured distally is divided by the ostium pressure and the result is defined as FFR (fractional flow reserve). FFR is an important measurement and may be used to determine if a stent should be inserted in an artery. Post-placement, FFR can also be obtained to determine if a stent has opened up a vessel sufficiently such that the treatment can be characterized as a success.

Stand-alone pressure wires are usually limited to a maximum diameter of 0.014" because larger pressure wires partially occlude the vessel in the stenotic region and cause an excessively large pressure drop. This large pressure drop prevents obtaining an accurate FFR measurement.

To correct for the partial occlusion caused by the introduction of the pressure wire through a stenosis it is important to understand the geometry of the vessel. One way to determine the geometry of the vessel is to image the vessel. Imaging can be performed using optical coherence tomography (OCT) such as with an OCT probe. OCT probes generally are placed over a guidewire. High-speed OCT probes typically include an external torsional transmission device disposed over a rotating optical fiber in order for the fiber to rotate uniformly.

In this case, the diameter of the torque wire has to be large to transmit torque over the entire length of the probe. The combination of a torque wire and an OCT probe would typically disturb any pressure measurement made with the OCT probe placed across a lesion in the vessel.

Accordingly, methods and devices are needed for improving pressure measurements that do not cause unwanted pressure drops or occlude the lumen being evaluated or that otherwise reduce or correct errors associated with intra-luminal pressure readings. Embodiments of the present invention address these needs and others.

SUMMARY OF THE INVENTION

In part, the invention relates to a method and apparatus for obtaining a corrected FFR in a vessel having a stenosis. In one aspect, the invention relates to an apparatus for measuring corrected FFR of a vessel having a stenosis. In one embodiment, the apparatus includes a probe comprising an OCT assembly and a pressure assembly, and a processor in communication with the OCT assembly and the pressure assembly.

In one embodiment, the pressure assembly measures values of pressure in predetermined locations in the vessel and communicates them to the processor. In another embodiment, the OCT assembly measures the geometry of the vessel in predetermined locations. In another embodiment, the processor determines the corrected FFR of the vessel in response to the geometry at the predetermined locations within the vessel and the pressure measured at predetermined locations in the vessel.

In another embodiment, the pressure is measured in the ostium and distal to the stenosis. In still another embodiment, initial FFR is calculated by dividing the pressure measured distal to the stenosis by the pressure measured in the ostium. In still yet another embodiment, the processor corrects the initial FFR using hydrodynamic equations and the geometry of the vessel as measured with OCT. In yet another embodiment, the processor calculates a damage index, such as for example a myocardial damage index. In one embodiment, the damage index is calculated as the ratio of the measured pressure drop to the expected pressure drop. In still yet another embodiment, the processor calculates the geometry of the lumen wall by estimating the wall geometry hidden from OCT imaging by a guide wire. In another embodiment, the processor calculates the corrected FFR iteratively.

In another aspect, the invention relates to a method of calculating a corrected FFR in a vessel having a stenosis. In one embodiment, the method includes the steps of measuring values of pressure in predetermined locations in the vessel, measuring the geometry of the vessel in predetermined locations; and calculating the corrected FFR of the vessel in response to the geometry at the predetermined locations within the vessel and the pressure measured at predetermined locations in the vessel. In another embodiment, the pressure is measured in the ostium and distal to the stenosis. In yet another embodiment, an initial FFR is calculated by dividing the pressure measured distal to the stenosis by the pressure measured in the ostium. In yet another embodiment, the method further includes the step of calculating the geometry of the lumen wall by estimating the wall geometry hidden from OCT imaging by a guidewire. In still yet another embodiment, the processor corrects the initial FFR using hydrodynamic equations and the geometry of the vessel as measured with OCT. In still yet another embodiment, the corrected FFR is iteratively obtained. In another embodiment, a damage index is calculated as the ratio of the measured pressure drop to the expected pressure drop.

In another aspect, the invention relates to a pressure sensing optical coherence tomography probe including an optical fiber capable of transmitting light of a first wavelength and second wavelength; an angled fiber adjacent to and coaxial with the optical fiber, the angled fiber capable of totally internally reflecting the first wavelength of light; and an optical pressure transducer, coaxial with the angled fiber and optical fiber and positioned distal to the angled fiber, the optical pressure transducer configured to modulate light of the second wavelength. In one embodiment, an angled fiber is a type of beam director. Other beam directors can be used in lieu of an angled fiber.

In one embodiment, the second wavelength passes through the angled fiber. In another embodiment, the optical pressure transducer and the angled fiber are positioned within a sheath. In yet another embodiment, a marker is positioned over a portion of the sheath. In still yet another embodiment, the probe includes a beam shaper and a beam expander positioned between the angled fiber and the optical fiber. In one embodiment, the probe includes a torque wire defining a lumen in which the optical fiber is disposed. In yet another embodiment, an air filled cavity is defined between the pressure transducer and the angled fiber.

In another aspect, the invention relates to a combination optical and pressure probe including an optical fiber capable of transmitting light of a first wavelength; an optical pressure transducer positioned coaxial with and adjacent to the optical fiber, the optical pressure transducer capable of modulating the light of the first wavelength; and the angled fiber positioned coaxial with and distal to the optical pressure transducer, the angled fiber configured to totally internally reflect the first wavelength of light. In one embodiment, the optical pressure transducer and the angled fiber are positioned within a sheath. In another embodiment, the combination probe includes a marker positioned over a portion of the sheath. In yet another embodiment, the combination optical and pressure probe includes an air gap formed between the sheath and the angled fiber.

In another embodiment, the combination probe further includes a beam shaper and a beam expander positioned between the optical pressure transducer and the optical fiber. In yet another embodiment, the combination probe includes a torque wire defining a lumen in which the optical fiber is disposed. In still yet another embodiment, the combination probe includes a gel disposed between the optical pressure transducer and the angled fiber. In another embodiment of the combination optical and pressure probe, the gel is in communication with a volume defined by the probe through a port defined within the sheath.

In another aspect, the invention relates to a combination optical and pressure catheter. In one embodiment, the catheter includes a catheter wall defining a lumen; an OCT optical probe movably positioned within the lumen; and an electrical pressure transducer positioned within a pocket within the wall of the catheter. In one embodiment, the electrical pressure transducer includes leads embedded in the wall of the catheter. In another embodiment, the electrical transducer is separated from the environment of the catheter by a gel positioned within the pocket in the wall of the catheter.

In another aspect, the invention relates to a torque wire assembly having a first torque wire having a first diameter joined to a second torque wire having a second diameter. In one embodiment, the first torque wire is joined to the second torque wire with a collar. In another embodiment, the torque wire assembly is welded to the collar. In yet another embodiment, the second torque wire is positioned within the collar. In still yet another embodiment, the length of the first diameter torque wire is substantially ten times the length of the second diameter torque wire. In another embodiment, the first diameter is greater than 0.5 mm and the second diameter is less than 0.35 mm. In yet another embodiment, the first torque wire abuts the second torque wire and the two torque wires are located within and held together by a tube. In still yet another embodiment, the torque wire assembly further includes a filler tube within the tube. The tube can be shrunk around the torque wires in one embodiment.

In another aspect, the invention relates to an OCT catheter having a torque wire defining a lumen; an optical fiber positioned within and extending from the torque wire; and a transition coating extending from the torque wire to the optical fiber at the position where the optical fiber exits the torque wire.

In still yet another embodiment, the invention relates to an OCT catheter. In one embodiment, the OCT catheter includes a first torque wire having a first diameter and defining a first lumen, a second torque wire having a second diameter and defining a second lumen, and an optical fiber, wherein the first and second torque wires are joined, and wherein the optical fiber passes through the first and second lumen. In one embodiment, the OCT catheter further includes a collar, wherein the collar joins and aligns the first and second torque wires. In yet another embodiment, the OCT catheter further includes a sheath covering the first and second torque wires and the optical fiber.

In another aspect, the invention relates to a system for determining a corrected fractional flow reserve of a vessel having a stenosis. The system includes a pressure assembly configured to measure pressures at predetermined locations in the vessel, an optical coherence tomography assembly configured to measure a geometry of the vessel at predetermined locations within the vessel, and a processor in communication with the optical coherence tomography assembly and the pressure assembly. The processor can be configured to execute a program to calculate the corrected fractional flow reserve for the vessel in response to the geometry at the predetermined locations within the vessel and the pressures measured at predetermined locations in the vessel.

In some embodiments of the system, the predetermined locations include an ostium of the vessel and distal to the stenosis in the vessel. In some embodiments, an initial fractional flow reserve is calculated by dividing the pressure measured distal to the stenosis by the pressure measured in the ostium. In some embodiments, the processor is configured to execute the program to correct an initial fractional flow reserve using hydrodynamic equations and the geometry of the vessel measured with the optical coherence tomography assembly. In some embodiments, the processor is configured to execute the program to output a myocardial damage index as a ratio of a measured pressure drop to an expected pressure drop. In some embodiments, the processor is configured to execute the program to model the geometry of the vessel by estimating a wall geometry hidden from optical coherence tomography imaging by a guidewire. In some embodiments, the system also can include a probe, wherein the optical coherence tomography assembly and the pressure assembly are disposed in the probe.

In some embodiments, the optical coherence tomography assembly is disposed in the probe. The optical coherence tomography assembly also can include an optical fiber. In addition, the probe can include a first torque wire having a first diameter and defining a first lumen, a second torque wire having a second diameter and defining a second lumen, wherein the first and second torque wires are joined, and wherein the optical fiber passes through the first lumen and the second lumen. In some embodiments, the optical coherence tomography assembly includes an optical fiber configured to transmit light of a first wavelength band and a second wavelength band; a beam director adjacent to and coaxial with the optical fiber, the beam director configured to reflect light of the first wavelength band. The pressure assembly has an optical pressure transducer, coaxial with the beam director and optical fiber, and positioned distal to the beam director, the optical pressure transducer configured to modulate light of the second wavelength band.

In another aspect, the invention relates to a method of determining a corrected fractional flow reserve in a vessel having a stenosis. The method includes the steps of: measuring values of pressure at predetermined locations in the vessel using a pressure assembly; determining a geometric boundary of the vessel at the predetermined locations using optical coherence tomography; and determining, using a processor, the corrected fractional flow reserve of the vessel in response to the geometric boundary measured at the predetermined locations within the vessel and the pressure measured at the predetermined locations in the vessel.

In some embodiments of the method, the pressure is measured in the ostium and distal to the stenosis in the vessel. In some embodiments, the step of determining the geometric boundary of the vessel includes the step of estimating a portion of the geometric boundary of the vessel hidden from optical coherence tomography imaging by a guidewire. In some embodiments, the method can include the step of iteratively obtaining the fractional flow reserve. In some embodiments, an initial fractional flow reserve is calculated by dividing the pressure measured distal to the stenosis by the pressure measured in the ostium. In some embodiments, the processor corrects an initial fractional flow reserve using three dimensional hydrodynamic equations and the geometric boundary of the vessel measured with optical coherence tomography. In some embodiments, a myocardial damage index is calculated as a ratio of a measured pressure drop to an expected pressure drop.

In another aspect, the invention relates to a method of evaluating stent placement in a vessel. The method includes the steps of: determining, using a processor, a first fractional flow reserve in the vessel prior to stent placement; correcting, using the processor, errors introduced by a first probe obstructing the vessel to determine a first corrected fractional flow reserve; determining, using the processor, a second fractional flow reserve in the vessel after stent placement; correcting, using the processor, errors introduced by an obstruction in the vessel to determine a second corrected fractional flow reserve; and comparing the first corrected fractional flow reserve and the second corrected fractional flow reserve.

In some embodiments of the method, the obstruction is the first probe or a second probe.

In some embodiments, the method includes the step of determining a level of effectiveness after stent placement in response to the step of comparing. In some embodiments, the method includes the step of outputting a damage index in response to the step of comparing.

In another aspect, the invention relates to a data collection probe. The probe includes an optical fiber configured to transmit light of a first wavelength band and a second wavelength band; a beam director adjacent to and coaxial with the optical fiber, the beam director configured to reflect light of the first wavelength band; and an optical pressure transducer, coaxial with the beam director and optical fiber and positioned distal to the beam director, the optical pressure transducer configured to modulate light of the second wavelength band.

In some embodiments of the data collection probe, the beam director is configured to transmit light of the second wavelength band. In some embodiments, the probe includes a sheath, wherein the optical pressure transducer and the beam director are positioned within the sheath. In some embodiments, the probe includes an angiography marker positioned over a portion of the sheath. In some embodiments, the probe includes a beam shaper and a beam expander positioned between the beam director and the optical fiber. In some embodiments, the probe includes a torque wire defining a lumen in which the optical fiber is disposed. In some embodiments, an air filled cavity is defined between the pressure transducer and the beam director. In some embodiments, the probe includes a purge assembly having a fluid restricting device and a purge fluid supply, the fluid restricting device in fluid communication with a purge port defined by the sheath. In some embodiments, the fluid restricting device is adjustable and can include a biasing element and a slidable member defining a hole, the hole positioned to received purge fluid from the purge fluid supply and the biasing element configured to apply a biasing force upon the slidable member.

In another aspect, the invention relates to a combination optical and pressure probe. The probe can include an optical fiber configured to transmit light of a first wavelength band; an optical pressure transducer positioned coaxial with and adjacent to the optical fiber, the optical pressure transducer capable of modulating the light of the first wavelength band; and a beam director positioned coaxial with and distal to the optical pressure transducer, the beam director configured to totally internally reflect the light of the first wavelength band.

In some embodiments of the combination optical and pressure probe, the optical pressure transducer and the beam director are disposed within a sheath. In some embodiments the probe can include a marker disposed over a portion of the sheath. In some embodiments, an air gap is formed between the sheath and the beam director. In some embodiments, the probe can include a beam shaper and a beam expander positioned between the optical pressure transducer and the optical fiber. In some embodiments, the probe can include a torque wire defining a lumen in which the optical fiber is disposed. In some embodiments, the probe includes a gel disposed between the optical pressure transducer and the beam director. In some embodiments, the gel can be in fluid communication with a volume defined by the probe through a port defined within the sheath.

In another aspect, the invention relates to a combination optical and pressure catheter. The catheter can include a wall of a catheter; a lumen defined by the wall; a rotatable optical fiber disposed within the lumen; and an electrical pressure transducer disposed within a pocket disposed in the wall.

In some embodiments of the combination optical and pressure catheter, the electrical pressure transducer includes leads embedded in the wall. In some embodiments, the electrical pressure transducer is separated from the lumen by a gel positioned within the pocket. In some embodiments, the catheter includes a beam director in optical communication with the rotatable fiber and wherein the size of the leads are configured to increase an amount of light entering the beam director.

In another aspect, the invention relates to a torque wire assembly. The torque wire assembly can include a first torque wire having a first diameter and a second torque wire having a second diameter, wherein the first torque wire is joined to the second torque wire.

In some embodiments of the torque wire assembly, the first torque wire is joined to the second torque wire with a collar. In some embodiments, the torque wire assembly can include an optical fiber, wherein the first torque wire defines a first axial bore and wherein the second torque wire defines a second axial bore, wherein the optical fiber is disposed in at least one of the first axial bore or the second axial bore. In some embodiments, the second torque wire is disposed within the collar. In some embodiments, the length of the first diameter is about ten times the length of the second diameter. In some embodiments, the first diameter is greater than about 0.5 mm and the second diameter is less than about 0.35 mm. In some embodiments, the first torque wire abuts the second torque wire and the first and the second torque wires are located within and held together by a tube heat shrunk around the first and second torque wires. In some embodiments, the torque wire assembly includes a filler tube disposed within the tube. In some embodiments, the torque wire assembly can include a sheath, wherein the optical fiber is in optical communication with an angled beam director and wherein the optical fiber is at least partially disposed in the sheath.

In another aspect, the invention relates to a torque wire assembly that can include a torque wire defining a lumen; an optical fiber positioned within the lumen and extending from the torque wire; and a protective coating extending from the torque wire to the optical fiber at a position wherein the optical fiber exits the torque wire.

In some embodiments of the torque wire assembly, the protective coating is a transition plastic. In some embodiments of the torque wire assembly, the torque wire and the optical fiber are coupled by an interference fit. In some embodiments of the torque wire assembly, the protective coating is a tube having an outer diameter. In some embodiments of the torque wire assembly, the outer diameter has a spiral shape configured to reduce non-uniform rotational distortion.

In another aspect, the invention relates to a torque wire assembly that can include a first torque wire having a first diameter and defining a first lumen, a second torque wire having a second diameter and defining a second lumen, and an optical fiber, wherein the first and second torque wires are joined, and wherein the optical fiber passes through the first lumen and the second lumen.

In some embodiments, the torque wire assembly can include a collar, wherein the collar joins and aligns the first and second torque wires. In some embodiments, the torque wire assembly can include a sheath covering the first and second torque wires and the optical fiber. In some embodiments, the first and second torque wires are coaxially aligned. In some embodiments, the torque wire assembly can include a metal collar, wherein the first and second torque wires are joined by a metal collar. In some embodiments, the optical fiber has an interference fit with at least one of the first torque wire or the second torque wire. In some embodiments, the sheath defines a purge port and includes a pressure transducer in fluid communication with the purge port. In some embodiments, the first diameter is reduced in size relative to the second diameter such that a pressure drop measured across a narrowed region of a blood vessel using the pressure transducer increases in accuracy in an amount proportional to the reduction in size of the first diameter. In one embodiment, the probe includes a catheter having a wall defining a lumen, and a purge port and further includes a fluid supply; a three way valve having a first port in communication with the lumen, a second port in communication with the fluid supply and a third port in communication with the pressure assembly, wherein the pressure assembly is a pressure transducer, wherein when in the first position the valve connects the fluid supply with the lumen, and wherein when in the second position the valve connects the lumen and the pressure transducer.

In another aspect, the invention relates to a pressure measuring apparatus. The pressure measuring apparatus can include a fluid delivery channel configured to deliver purge solution to a purge port in a data collection probe; a fluid supply in fluid communication with the purge port; a pressure transducer in fluid communication with the fluid delivery channel; and a valve in fluid communication with the fluid supply and the pressure transducer.

In some embodiments, the pressure measuring apparatus can include a data collection probe. In some embodiments, the data collection probe can include a catheter having a wall defining a lumen and the purge port and a rotatable optical fiber disposed in the catheter. In some embodiments, the valve is a three-way valve having a first port in communication with the lumen, a second port in communication with the fluid supply and the third port in communication with the pressure transducer. In some embodiments, the three-way valve is configured such that when in the first position the three-way valve connects the fluid supply with the lumen, and when in the second position the three-way valve connects the lumen and the pressure transducer. In some embodiments, the pressure measuring apparatus can include a signal conditioning circuit in electrical communication with the pressure transducer. In some embodiments, the pressure measuring apparatus can include a wireless transceiver in electrical communication with the signal conditioning circuit. In some embodiments, the pressure measuring apparatus can include an optical coherence tomography system having an optical coherence tomography system transceiver, the optical coherence tomography system transceiver in electrical communication with the wireless transceiver. In some embodiments, the optical coherence tomography system transceiver is in electrical communication with the wireless transceiver. In some embodiments, the pressure transducer is in fluid communication with and disposed between the purge port and the fluid supply. In some embodiments, the pressure transducer is in fluid communication with the lumen and disposed in the data collection probe. In some embodiments, the pressure measuring apparatus can include a fluid control device in fluid communication with the purge port and disposed between the fluid supply and the pressure transducer. In some embodiments, the pressure measuring apparatus can include a restriction configured to control a rate of flow of purge solution, wherein the restriction comprises a gap defined by the rotatable optical fiber and the wall, the restriction in fluid communication with the purge port.

In another aspect, the invention relates to a method of measuring pressure in a blood vessel. The method can include the steps of collecting pressure data using a pressure transducer in fluid communication with a purge port of a probe, the purge port disposed in the blood vessel at a first location; collecting optical coherency tomography data with respect to the blood vessel after initiating a purge; and outputting a pressure-based measurement with respect to the first location, using a processor, in response to the collected pressure data.

In some embodiments, the method of measuring can include the step of stabilizing the pressure data measured using the pressure transducer. In some embodiments, the step of stabilizing includes controlling flow of purge solution relative to the pressure transducer. In some embodiments, the method of measuring can include the step of reducing a damping level of the pressure transducer, wherein the probe is an optical tomography probe. In some embodiments, the step of reducing a damping level includes maintaining a substantially constant level of purge solution flow in line with the pressure transducer during a data collection period. In some embodiments, the method of measuring can include the steps of connecting a respective port of a three port valve to a fluid reservoir; to a lumen of the probe; and to the pressure transducer; setting the three port valve to a first position connecting the fluid reservoir to the lumen of the probe and purging the lumen of air; placing the probe in the blood vessel of interest and moving the probe into the vessel such that the purge port is positioned beyond a stenosis; and setting the three port valve to a second position connecting the pressure transducer to the lumen of the probe.

In another aspect, the invention relates to a purge system. The purge system can include a fluid supply configured to deliver a purge solution; a check valve in fluid communication with the fluid supply; a fluid flow control device in fluid communication with the check valve; and a fluid delivery channel configured to transport the purge solution to a data collection probe having a purge port.

In another aspect, the invention relates to a pressure measuring catheter apparatus. The apparatus can include a catheter having a wall defining a lumen and a purge port and a fluid filing port; a fluid supply; a pressure transducer; and a three way valve, the three way valve having a first port in communication with the lumen, a second port in communication with the fluid supply and the third port in communication with the pressure transducer, wherein when in the first position the valve connects the fluid supply with the lumen, and wherein when in the second position the valve connects the lumen and the pressure transducer. The apparatus can further include a signal conditioning circuit in electrical communication with the pressure transducer. The apparatus can further include a wireless transceiver in electrical communication with the signal conditioning circuit. The apparatus can further include an OCT system comprising an OCT system transceiver, the OCT system transceiver in electrical communication with the apparatus transceiver. In one embodiment, the OCT system transceiver in electrical communication with the apparatus transceiver is in communication wirelessly.

In another aspect, the invention relates to method for measuring pressure in a vessel. The method can include connecting a respective port of a three port valve to a fluid reservoir; to a lumen of a catheter defining a purge port; and to a pressure transducer; setting the three port valve to a first position connecting the fluid reservoir to the lumen of the catheter defining the purge port and purging the lumen of air; placing the catheter in the blood vessel of interest and moving the catheter into the vessel such that the purge port is positioned beyond the stenosis; setting the three port valve to a second position connecting the pressure transducer to the lumen of the catheter defining the purge port; and measuring the pressure using the pressure transducer.

In some embodiments of the purge system, the fluid control device is in fluid communication with the purge port and disposed between the fluid supply and the fluid delivery channel. In some embodiments, the fluid control device is selected from the group consisting of a restriction, an adjustable restriction, an expandable tube, and an expandable tube disposed in an expansion limiter. In some embodiments, the fluid control device includes an expansion limiter and an expandable tube having a first opening and a second opening, the expansion limiter at least partially surrounding the expandable tube. In some embodiments, the purge system can include a fluid restricting element. In some embodiments, the fluid restricting element is configured to have a fixed restriction. In some embodiments, the fluid restricting element is an adjustable restriction apparatus. In some embodiments, the adjustable restriction apparatus includes a biasing element and a plug, and a housing defining a bore, the biasing element slidably disposed relative to the plug. In some embodiments, the biasing element is a spring configured to compress in response to an applied pressure from the purge solution.

In some embodiments, the purge system can include a data collection probe, the probe having a sheath, the purge port defined by the sheath, the data collection probe having a rotatable optical fiber disposed in the sheath. In some embodiments, the purge system can include a pressure transducer disposed between the fluid supply and the fluid delivery channel. In some embodiments, the fluid control device is configured to maintain a substantially constant level of purge solution flow during a purge of the data collection probe. In some embodiments, the purge system can include a signal conditioner in fluid communication with the pressure transducer.

In another aspect, the invention relates to a method of purging a data collection probe. The method can include expanding a flexible elongate tube upon receiving a purge solution; constraining expansion of flexible elongate tube; expelling the received purge solution stored in expanded flexible elongate tube; and transporting the expelled purge solution to a purge port of the data collection probe.

In some embodiments, the method of purging can include collecting optical coherence data with the data collection probe. In some embodiments, the method of purging can include transporting purge solution through a check valve prior to expanding the flexible elongate tube. In some embodiments, the method of purging can include maintaining a substantially constant level of purge solution flow during a purge of the data collection probe. In some embodiments, the method of purging can include restricting flow of the expelled purge solution using a restriction element. In some embodiments, the method of purging can include returning the flexible elongate tube to an unexpanded state when an applied pressure of the purge solution drops below a threshold value. In some embodiments, the method of purging can include adjusting flow of the expelled purge solution through the restriction element.

In one embodiment, the invention relates to a data collection system. The system includes a pressure assembly configured to measure pressure at one or more predetermined locations in a vessel, and an optical coherence tomography assembly configured to measure a geometry of the vessel at one or more of the predetermined locations within the vessel. The system can further include a probe. The optical coherence tomography assembly can be disposed in the probe. In one embodiment, the optical coherence tomography assembly can include an optical fiber, wherein the probe further includes a first torque wire having a first diameter and defining a first lumen and a second torque wire having a second diameter and defining a second lumen, wherein the first and second torque wires are joined, and wherein the optical fiber passes through the first lumen and the second lumen.

In one embodiment, the system can further include a probe, wherein the optical coherence tomography assembly is disposed in the probe, the optical coherence tomography assembly can include an optical fiber configured to transmit light of a first wavelength band and a second wavelength band; and a beam director adjacent to and coaxial with the optical fiber, the beam director configured to reflect light of the first wavelength band, wherein the pressure assembly can include an optical pressure transducer, coaxial with the beam director and the optical fiber, and positioned distal to the beam director, the optical pressure transducer configured to modulate light of the second wavelength band.

In one embodiment, the system can further include a processor in communication with the optical coherence tomography assembly and the pressure assembly, the processor configured to execute a program to calculate a corrected fractional flow reserve for the vessel in response to the geometry at one or more of the predetermined locations within the vessel and the pressure measured at one or more predetermined locations in the vessel. In one embodiment, the processor is configured to execute the program to correct an initial fractional flow reserve using hydrodynamic equations and the geometry of the vessel measured with the optical coherence tomography assembly. In one embodiment, the processor is configured to execute the program to output a myocardial damage index as a ratio of a measured pressure drop to an expected pressure drop. The system can further include a purge assembly that includes a fluid restricting device and a purge fluid supply, the fluid restricting device in fluid communication with a purge port defined by a wall of the probe. In one embodiment, the fluid restricting device is adjustable and includes a biasing element and a slidable member defining a hole, the hole positioned to received purge fluid from the purge fluid supply and the biasing element configured to apply a biasing force upon the slidable member. An air filled cavity can be defined between the pressure transducer and the beam director. The system can further include, in one embodiment, a wall of the probe; and a lumen defined by the wall, wherein the optical coherence tomography assembly comprises a rotatable optical fiber disposed within the lumen and wherein the pressure assembly comprises a pressure transducer disposed within a pocket disposed in the wall.

In one embodiment, the pressure transducer can be separated from the lumen by a gel positioned within the pocket. The system can further include a fluid supply configured to deliver a purge solution; a check valve in fluid communication with the fluid supply; a fluid flow control device in fluid communication with the check valve; and a fluid delivery channel configured to transport the purge solution to a purge port defined by a wall of the probe. In one embodiment, the fluid control device is selected from the group consisting of a restriction, an adjustable restriction, an expandable tube, and an expandable tube disposed in an expansion limiter. In one embodiment, the length of the first diameter is about ten times the length of the second diameter. In one embodiment, the first torque wire abuts the second torque wire and the first and the second torque wires are located within and held together by a tube heat shrunk around the first and second torque wires.

In another aspect, the invention relates a processor-based method of determining one or more parameters of a vessel based on measured optical data and measured pressure data. The method includes measuring a pressure value at one or more predetermined locations in the vessel using a pressure assembly; determining a geometric boundary of the vessel at the one or more predetermined locations using an optical coherence tomography assembly; and determining, using a processor, a fractional flow reserve of the vessel in response to the geometric boundary measured at the one or more predetermined locations within the vessel and the measured pressure value at the one or more predetermined locations in the vessel. In one embodiment, the step of determining the geometric boundary of the vessel comprises the step of estimating a portion of the geometric boundary of the vessel hidden from optical coherence tomography by a guidewire.

In one embodiment, the method further includes the step of iteratively obtaining the fractional flow reserve such that one or more corrections are made to reduce errors associated with using the pressure measuring assembly and the optical coherence tomography assembly in the vessel. The method can further include the step of determining an initial fractional flow reserve by dividing a first pressure measured distal to a stenosis by a second pressure measured in an ostium. In one embodiment, the processor further determines the fractional flow reserve by correcting an initial fractional flow reserve using three dimensional hydrodynamic equations and the geometric boundary of the vessel measured with the optical coherence tomography assembly.

In one embodiment, the step of determining, using a processor, a fractional flow reserve further includes determining, using a processor, a first fractional flow reserve in the vessel; correcting, using the processor, errors introduced by a first probe obstructing the vessel to determine a first corrected fractional flow reserve; determining, using the processor, a second fractional flow reserve in the vessel; correcting, using the processor, errors introduced by an obstruction in the vessel to determine a second corrected fractional flow reserve; and comparing the first corrected fractional flow reserve and the second corrected fractional flow reserve. In one embodiment, the obstruction is the first probe, a second probe, a stenosis or a stent. The method can further include the step of outputting a damage index in response to the step of comparing. In one embodiment, the pressure measuring assembly and the optical coherence tomography assembly are disposed in the first probe. In one embodiment, the pressure assembly is a pressure transducer in fluid communication with a purge port of a catheter disposed in the vessel and wherein the pressure value is measured at a predetermined location near the purge port.

This Summary is provided merely to introduce certain concepts and not to identify any key or essential features of the claimed subject matter.

DESCRIPTION OF THE DRAWINGS

The objects and features of the invention can be understood more completely by referring to the drawings described below and the accompanying descriptions. In the drawings, like numerals are used to indicate like parts throughout the various views.

FIG. 4 is a diagram of a torque wire according to an illustrative embodiment of the invention.

FIG. 5 is a diagram of longitudinal-section of the embodiment of the torque wire of FIG. 4.

DETAILED DESCRIPTION

U.S. patent application having Publication No. 2011-0071404 assigned to the owner of this application and herein incorporated by reference in its entirety describes a method of calculating a pressure drop in a lumen and related methods of obtaining FFR (fractional flow reserve). A data collection probe, such as an OCT probe, a pressure data probe or other probes suitable for collecting data used to measure or determine FFR or related parameters can be used as described herein. In one embodiment, when collecting data with respect to a blood vessel, the data collection probe is disposed in the lumen of the vessel.

In brief overview, one method for calculating a pressure drop in a lumen and measuring a fractional flow reserve (FFR) requires that the pressures measured within the vessel distal to a stenotic region be corrected for the effect of the probe partially obstructing flow through a stenotic region. To do this, an OCT image is made of the stenosis; an estimate of the unstenosed flow is made based on the largest diameter encountered within the stenotic region and then, using the geometry of the vessel as determined from the OCT image, a fluid dynamic simulation of unstenosed flow through the region is computed. One output of the fluid dynamic simulation computation is an estimate of the pressure along the artery. The geometry of the vessel can include, without limitation, one or more distance measurements of the vessel such as a radius, diameter, circumference, length, or thickness of the vessel, the vessel wall, a cavity or a volume defined thereby or a portion of any of the foregoing.

This method is somewhat limited because if the vessel is stenosed along its entire length, the assumed reference diameter will be underestimated, as will be the effect of the stenosis addition. If the vessel is supplying blood to part of the heart that has lost function due to an ischemic event, the contribution of the stenosis will be overestimated because there will be in actuality less flow to a damaged section of the heart.

Figure 1:
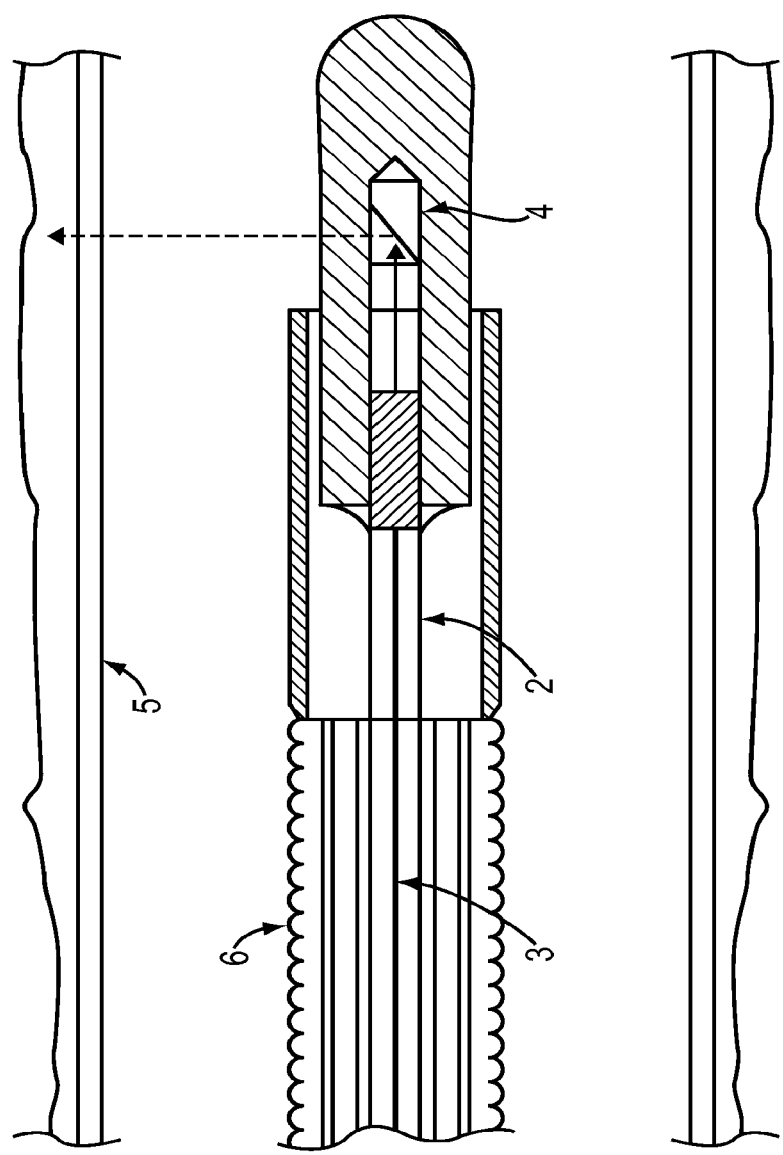
FIG. 1 is a highly schematic diagram of an OCT catheter according to an illustrative embodiment of the invention.

Referring to FIG. 1, one embodiment of an OCT catheter used in viewing the walls of a blood vessel includes an optical core 2 that includes an optical fiber 3 and a beam director 4, and that rotates within a sheath 5. The optical core 2 is driven by a torque wire 5 such that light emitted from a source (not shown) and passing through the optical fiber 3, is directed by the beam director 4, through the wall of the sheath 4 to the blood vessel wall. The light reflected by the blood vessel wall reenters the probe and is redirected by the beam director 3 back through the optical fiber 3 to detection electronics (also not shown). In order to obtain a better image, the lumen of the catheter is filled with a liquid having a refractive index which is close to the index of refraction of the liquid in the blood vessel whose walls are being imaged. The OCT catheter also includes a lumen for containing a guidewire 6 that permits the OCT pressure sensing catheter move to the site of interest in the vasculature of the patient. A pressure sensing OCT catheter also includes a pressure sensor, about which more will be said shortly.

Figure 1A:
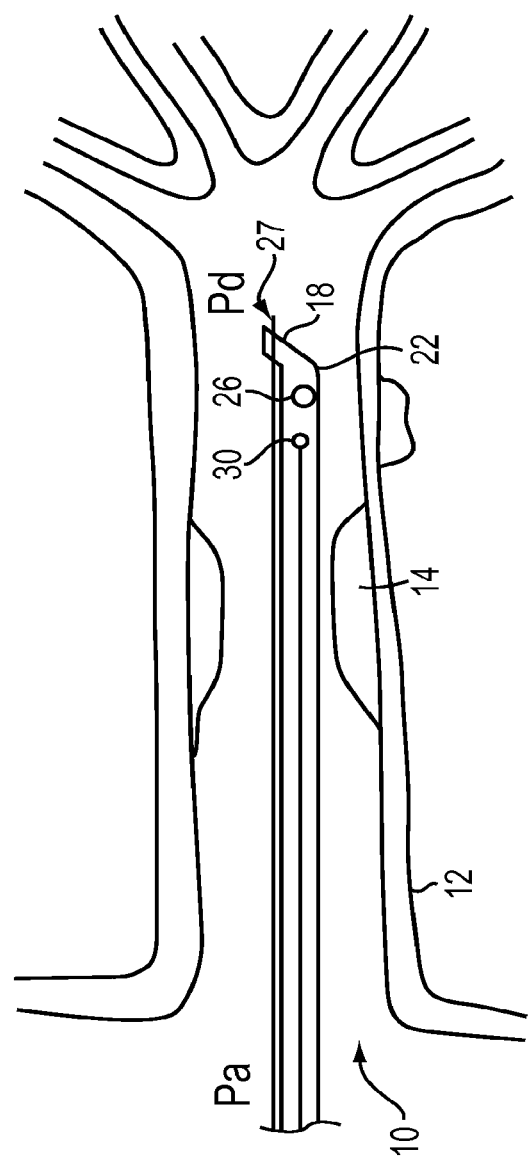
FIG. 1A is a highly schematic diagram of a pressure sensing OCT probe positioned in a stenotic vessel according to an illustrative embodiment of the invention.

Referring to FIG. 1A, as in the standard technique, hyperemia is induced using adenosine and the aortic pressure ($P_a$) at the ostium 10 or opening to the vessel 12 and the pressure distal ($P_d$) to the stenosis 14 is measured. The difference between these pressures is a direct measurement of the severity of the stenosis. As shown in FIG. 1A, the guidewire 18 and OCT pressure sensing catheter (or probe) 22 have to cross the stenotic lesion 14 to obtain the distal pressure measurement ($P_d$). The pressure transducer 26 and the OCT beam director 30 must both be distal to the stenotic lesion 14 for this data collection process to function. In one optional embodiment, the pressure transducer 27 is separate from but is near to the OCT probe. The volume and geometry of the catheter 22 adds a significant blockage to the stenosis and detrimentally affects the pressure reading. This in turn reduces the confidence in any derived FFR values. Fortunately, the acquisition of the OCT image allows a way to correct for the pressure reading error.

Figure 2:
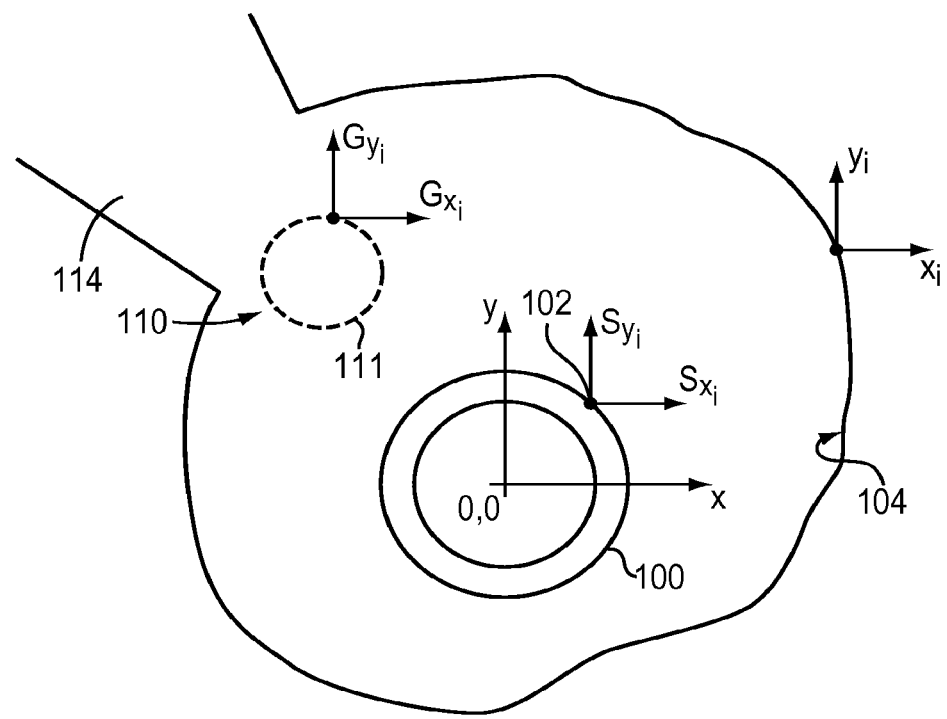
FIG. 2 is a schematic diagram of a cross-section of a vessel with a probe positioned within it and showing the coordinate systems used to perform various calculations and analyses according to an illustrative embodiment of the invention.

As shown in FIG. 2, a representation of an OCT image shows the sheath 100, the lumen wall 104, the guidewire 110, and the guidewire shadow 114. The OCT software locates the lumen wall 104 and assigns coordinates ($X_i$, $Y_i$) to it along the entire wall perimeter. The luminal contour is any possible grouping of one or more contour segments defining the lumen wall. In one embodiment, the longest valid segment is defined as the root (first segment to add to the contour) of the contour. The nearest clockwise and counter-clockwise neighboring segments of each potential contour segment are next identified. To be deemed valid (that is connectable to neighboring segments) neighboring segments must pass an angular distance threshold (how much of an arc is subtended), a radial distance threshold (how far away from the center is the segment), and a Euclidian (direct connection) distance threshold. Each potential contour is then traversed clockwise and counter-clockwise and the longest resulting contour is selected as the outline.

Missing contour data is next interpolated. In one embodiment, a smooth curve between two points is interpolated using a cosine function. The range of values of a standard cosine is +1 to −1, inclusive, in the domain 0 to $\pi$. Since the interpolation between two points requires a weighting range from 0 to 1 inclusive, rather than −1 to +1, it is desirable to adjust the cosine range. Using the function (1-cos) provides a range from 0 to 2 inclusive and dividing that function by 2, yields (1-cos)/2 with the required range from 0 to 1.

Alternatively, one can use any suitable function, such as the cubic function or the Hermite function, to interpolate missing data using four or more control points instead of two. Interpolating a point between two points $y_1 = f(x_1)$ and $y_2 = f(x_1 + \Delta x)$, calculates the value of the point on a preselected curve between $x_1$ and $x_2$. The general relation is given by $(1-\alpha)y_1 + (\alpha)y_2$, where $\alpha$ is the interpolation weight ranging from 0 at $x_1$ to 1 at $x_1 + \Delta x$. Using the previously described cosine weighting method, the weight of a point at given distance d from $x_1$ is calculated by $\alpha = (1-\cos(\pi * d / \Delta x))/2$. It should be noted that this invention is not limited to any one particular interpolation method.

By estimating position of the wall lumen, the perimeter of the lumen or the vessel may be completed or closed behind the guidewire shadow. The coordinates of the vessel wall are measured relative to the lens which is located at X=0, Y=0. In the present invention, the sheath outer diameter 102 is found and defined by a set of X, Y-coordinates $S_{xi}$, $S_{yi}$. Generally the sheath 100 is concentric or coaxial with the lens but the identification of the sheath outer diameter (OD) allows for more precision in the case where the sheath 100 is eccentric from the lens. In the present invention, the guidewire 110 location is also identified. Since the guidewire 110 is opaque, the OCT imaging probe cannot see through it and only the edge 111 closest the OCT lens is identified.

Figure 3:
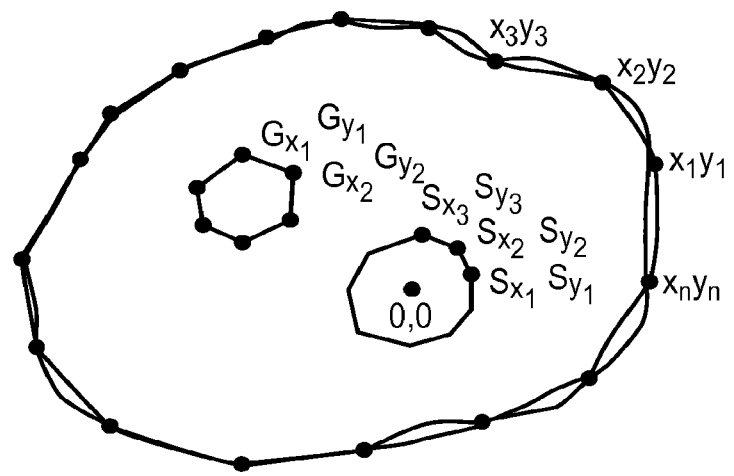
FIG. 3 is a schematic diagram of a cross-section of a vessel with a probe positioned within it and showing the approximate shape of the lumen as determined using line segments according to an illustrative embodiment of the invention.

In the present invention, this known edge is estimated as a segment of a circle of a predetermined diameter (in one embodiment about 0.014" diameter), the guidewire diameter for which the catheter was intended to be used. The location of points on the circumference of the circle $G_{xi}$, $G_{yi}$ defining the guidewire relative to the OCT lens is the defined. This process of estimating the lumen perimeter behind the guidewire and estimating the position and shape of the guidewire is repeated for each of the frames of the OCT image. As shown in FIG. 3, the coordinates of the sheath $X_i$, $Y_i$, the probe $S_{xi}$, $S_{yi}$, and the guidewire $G_{xi}$ and $G_{yi}$ are input values into the 3D computational fluid dynamics program, and the boundaries of the sheath and guidewire are approximated as discrete connected line segments. The pressure drop with the guidewire 18 and catheter 22 in place ($P_c$) is then calculated by the fluid dynamics program as is known to the art. This pressure $P_c$ is compared to $P_a - P_d$ obtained from the measurements by the pressure probe.

Once the cross-sectional area of the vessel has been determined, the severity of any stenotic region is then characterized. One measure of severity of a stenotic lesion imaged by OCT is provided by a parameter called the vascular resistance ratio (VRR). The VRR quantifies the blood flow resistance of a stenotic vessel segment relative to the flow resistance of the entire vessel branch, assuming maximum vasodilation of the peripheral coronary vasculature. The VRR is defined as:

$$VRR \equiv \frac{R_s}{R_T} \qquad (1)$$

where $R_s$ is the blood flow resistance of the stenotic segment and $R_T$ is the total flow resistance of the branch vessel in which the stenotic region is located. VRR ranges from 0 (no vessel narrowing) to 1 (all flow resistance due to the stenosis).

The calculation of VRR is based on a lumped parameter model of the blood flow through a stenosed branch of a coronary artery under hyperemic conditions. In this model, the blood flow Q, driven by the difference between the arterial blood pressure $P_a$ and the coronary venous pressure $P_v$, is limited by the total flow resistance ($R_T$) of the branch of the vessel through which the blood is flowing. $R_T$ is composed of the sum of three resistance elements, $$R_T = R_s + R_e + R_{mv} \qquad (2)$$

where $R_s$ is the blood flow resistance of the stenotic segment, $R_e$ is the blood flow resistance of the remaining epicardial length of the branch, and $R_{mv}$ is the microvascular resistance of the peripheral coronary vascular bed.

In general, the values of all three resistance elements depend on blood flow, but only $R_s$ is considered here to depend substantially on Q, because $R_{mv}$ and $R_e$ are only weakly flow-dependent under conditions of maximum vasodilation. During drug-induced hyperemia, $R_{mv}$ is approximately constant and is given by:

$$R_{mv} = \frac{P_a - P_v}{Q_{max}} \qquad (3)$$

Where $Q_{max}$ is the maximum blood flow that can be achieved in the branch when the pressure drop across the epicardial arteries is negligible (i.e., $R_s + R_e \rightarrow 0$). $Q_{max}$ equals the product of the mean hyperemic Doppler blood velocity, $v_{max}$, measured in a normal reference segment of the artery and the cross-sectional area, $A_n$, of the artery measured in the same location, $Q_{max} = v_{max} A_n$. Velocity may also be measured using speckle caused by particulates in the stream and detected in the OCT image. Based on these relationships, Eqn. 3 can be re-formulated in terms of hyperemic velocity:

$$R_{mv} = \left(\frac{P_a - P_v}{v_{max}}\right) \cdot \frac{1}{A_n} \qquad (4)$$

The quantity in braces, which has units of mm Hg cm$^{-1}$s, is the hyperemic microvascular resistance index, designated as H_mrv. An important advantage of determining hyperemic resistance using velocity instead of flow is that velocity normalizes flow for differences in arterial diameter due to branching and is preserved between proximal and distal segments. The values lie within a relatively narrow range for both treated and untreated vessels. The estimated flow ($F_{est}$) is based on the largest imaged area of the vessel ($A_i$).

$$F_{est} = A_i / H\_mrv \qquad (5)$$

H_mrv is obtained from physiological measurements of similar vessels. The vessels may be classified based on the artery, how distal or proximal the scan is in the artery, the patient height, the estimated weight of the heart, the patient's gender and an estimate of the overall disease state of the artery. $A_i$ is generally based on the largest imaged area of the vessel. However, with positive vessel remodeling it is possible that the largest vessel area may not represent the true vessel size. $A_i$ may also be estimated by summing up the areas of the branches and the distal end of the stenosis. Murray's law may be used in calculating this sum. $A_i$ may also be based on the average area in the pullback or areas of the branches taken from angiography.

This value of H_mrv is used in the simulation as the guessed value, $H\_mrv_{guess}$. It is adjusted upwards or downwards to give a new value ($H\_mrv_{corrected}$) according to:

$$H\_mrv_{corrected} = H\_mrv_{guess} \times (P_a - P_d)/P_c \qquad (6)$$

This value of $H\_mrv_{corrected}$ is iteratively reapplied to the hydrodynamic simulation until the measured pressure drop ($P_a-P_d$) is equal to the calculated value ($P_c$) within a predefined error limit. In one embodiment, the limit is reached when the new iterated value differs from the previous value by 0.001%. In one embodiment, the difference between the new iterated value and the previous value can range from above zero to about 10% of the previous value. When the difference between the iterated value and the previous value is within a predetermined limit, such as for example, the range referenced above, the iteration can be defined to have converged. The process of making this iterative solution converge may be sped up by using more sophisticated algorithms that take into account the expected shape of the pressure—flow curve of the stenosis. These include the effects of turbulence and the non-zero pressure at zero flow. Sophisticated search algorithms of the successive pressures may also be used to speed convergence. These include the Powell Search Algorithm and Linear Extrapolation.

Routines that cause the measured and calculated values to converge faster than a full computational fluid dynamics simulation routine may also be used. These include the lumped parameter algebraic methods. Given the additional information obtained from a pressure wire in some embodiments, the algebraic methods and other computer-based approximations or other methods can be used to perform the extrapolation and other iterative calculations described herein within the predefined error limit.

Once $H\_mrv_{corrected}$ is established, the catheter geometry $S_{xi}$, $S_{yi}$ is removed from the fluid dynamics simulation and the simulation rerun. The pressure drop obtained from the simulation then is directly comparable to the pressure drop of a pressure wire the size of guidewire. With this corrected pressure drop available, the common treatment decision point of FFR<0.75 may then be applied with more confidence.

In another embodiment, another calculation technique would also remove the guidewire geometry $G_{xi}$, $G_{yi}$ from the simulation. Although this would more accurately reflect the severity of the lesion, there is no clinical yardstick for pressure drop values without a guidewire. If such a yardstick is developed, the calculation including the removal of the guidewire would be a more accurate simulation.

When the pressure is obtained from an extrapolation, this can be a cause for concern. However, if the size of the combination OCT/FFR catheter is close to the size of the guidewire, the extrapolation error will not be significant when used in vessels with intermediate sized lesions.

Vessels with large lesions still benefit from the addition of the pressure transducer to an OCT probe or used with the OCT probe. If there is not a large pressure drop associated with a large lesion, this result indicates that the myocardium supplied by the imaged artery is severely compromised. The ratio of the measured pressure drop to the expected pressure drop can be defined as a damage index such as the myocardial damage index:

$$\text{Damage index}(Di) = (P_a - P_d)/P_c \qquad (7)$$

Arteries with small lesions also benefit from the addition of the pressure transducer to an OCT probe. The pressure transducer gives an accurate indication of the pressure drop in the artery and helps determine the overall physiologic affect which is useful in determining the disease state of the heart.

In order to reduce the effect of the probe on the pressure drop across the lesion, the wires and probes should be as small as possible. Some smaller OCT probes have a 2.7 F lesion crossing profile. This large size is driven by two factors: the size of the torque wire and the size of the lens. Both of these can be reduced in the section of the catheter that crosses the lesion.

A torque wire should be able to rotate within the catheter with minimal non-uniform rotational distortion (NURD) caused by the flexing of the wire during rotation. The current state of the art uses a dual layer torque coil. The NURD associated with torque wires with an outer OD below 0.020" is currently too high for obtaining precision images.

Assuming the shear force caused by the rotation of the imaging core in a liquid is uniform along the catheter length, which is true if there are no diameter transitions, the torque transmitted along the torque wire decreases linearly from its maximum value at the proximal end of the catheter to about zero at the distal end of the imaging core. Having a larger torque on the proximal end provides more energy transfer to where it is the most needed at the distal end.

One embodiment of a torque wire which will reduce the pressure drop caused by the wire itself is shown in FIG. 4. In one embodiment, there is a single reduction in the torque wire diameter. As shown in FIG. 4, a single reduction in diameter occurs between two torque wires 120 and 124, the larger diameter torque wire being proximal. In this embodiment, the coupling of the two torque wires 120 and 124 is performed at a metal join 128. When used in an OCT catheter, the optical fiber 132 (FIG. 5) runs through the middle of the torque wires 120, 124. For other catheters, wires or other signal transmission devices may run through the center of the torque wires 120, 124. A requirement of the coupling used to join the torque wires 120, 124 is to keep the two torque wires 120,124 coaxially aligned with each other.

One embodiment of the join 128 is shown in FIG. 5. A metal collar 128 whose outside diameter matches the larger torque wire 120 is butt welded to the larger torque wire 120. The inner diameter of the collar 128 is chosen to be slightly larger than the outer diameter of the smaller torque wire 124, allowing the smaller torque wire 124 to slide into the collar 128. In one embodiment, the larger diameter is greater than about 0.5 mm and the smaller diameter is less than about 0.35 mm. The smaller torque wire 124 is then glued or welded to the collar 128. In one embodiment, each wire of the smaller torque wire is about 0.001" in diameter and is wrapped in a dual layer, counter-wound configuration with four to eight fila per layer. The result is a centered and aligned join with a very short non-flexible section centered at the collar 128. A longer stiff section would create difficulties in allowing the catheter to navigate tortuous geometries, especially when the joint is located near the distal end.

Figure 6:
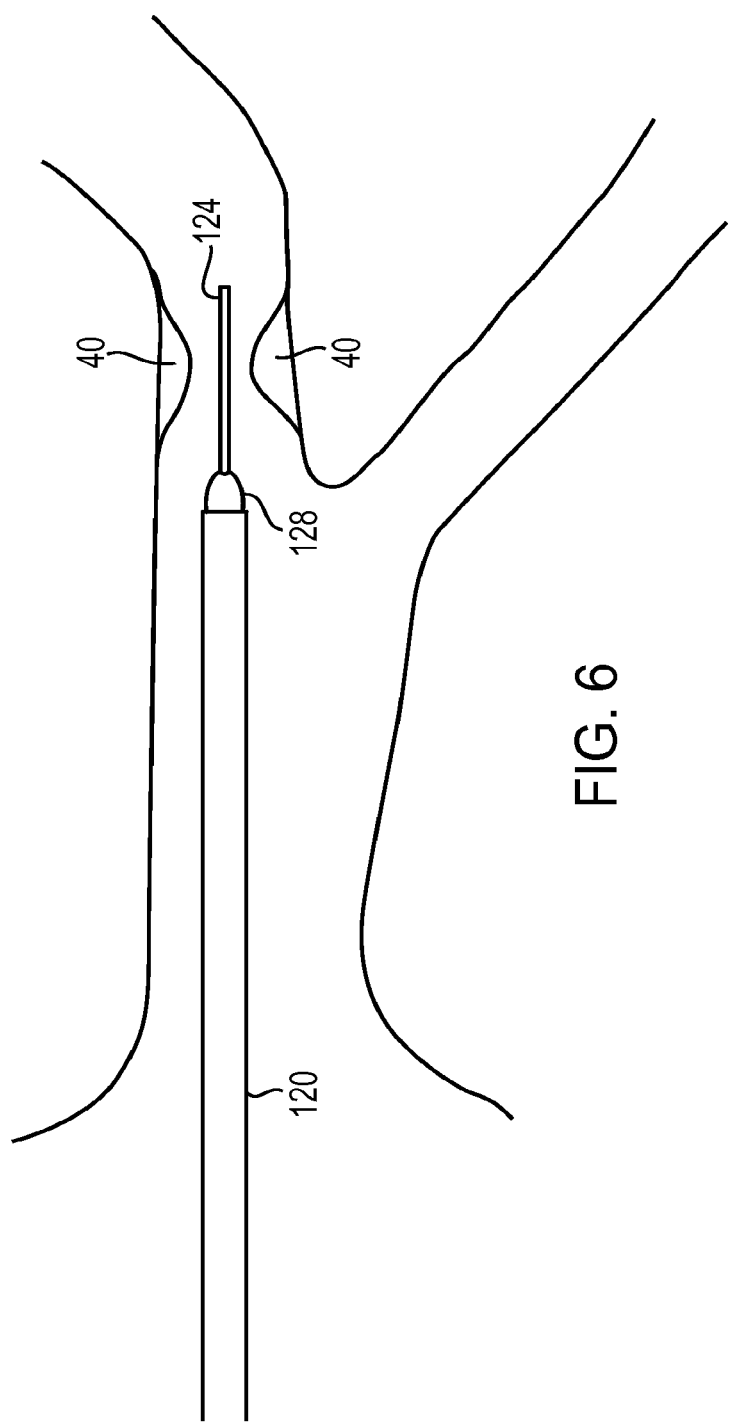
FIG. 6 is a view of an embodiment of an OCT/pressure probe embodiment in place in a stenotic region of a vessel.

The location of the joint may be anywhere along the catheter. In one embodiment (FIG. 6), the joint or collar 128 is located proximal to the section of the catheter that will enter a stenotic region 40. With this configuration the larger, more robust torque wire 120 will be able to transmit torque over most of the catheter length and the smaller torque wire 124 will be present where it is most critical for the diameter of the catheter to be small.

Figure 7:
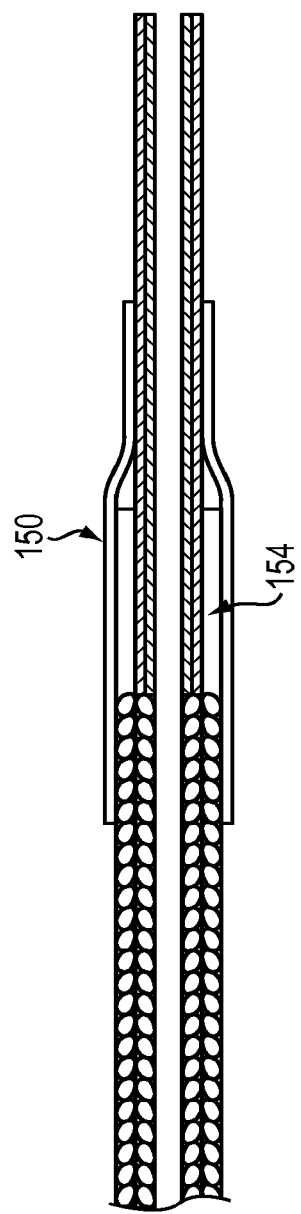
FIG. 7 is a longitudinal cross-section of another embodiment of a torque wire.

Another embodiment of a dual-torsion wire catheter or torque wire assembly is shown in FIG. 7. In this embodiment, heat-shrinkable tubing 150, composed of a material such as PET or Teflon, spans both torque wires. A filler material cylinder 154 keeps the torque wires centered and aligned. Other methods that are able to withstand the torque delivery requirements and keep the torque wires aligned may also be used.

Figure 8:
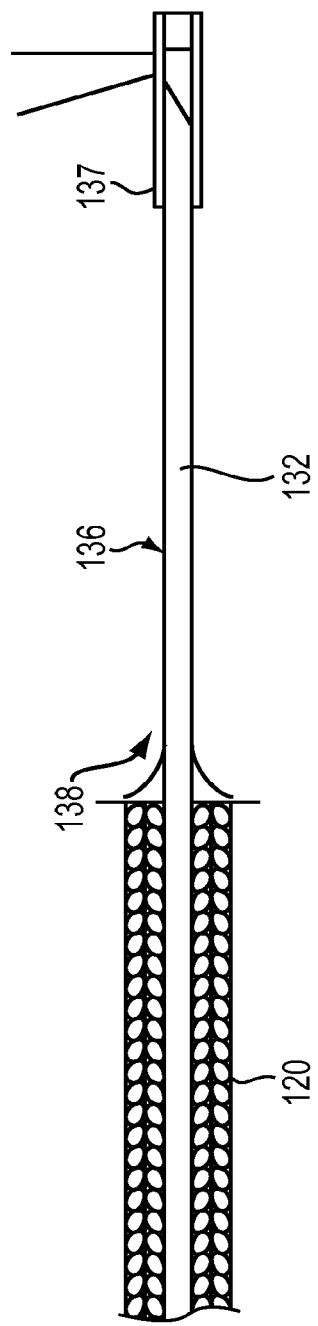
FIG. 8 is a longitudinal cross-section of yet another embodiment of a torque wire.

Because the distal section of the catheter is short, the use of a torque wire is not an absolute necessity because a mild degradation of image quality due to NURD over the short distance will not greatly affect performance. As shown in FIG. 8, a bare fiber 132 may be used over short distances as a torque transmission device. A protective cover or layer 138, such as a transition plastic, covers the termination of the torque wire 120 to smooth the transition at the end of the torque wire 120. Although this configuration is somewhat fragile, it is able to transmit sufficient torque through the optical fiber 132 to cause the lens assembly 137 to rotate at the desired speed. Other embodiments include placing heat-shrinkable tubing 136 over the bare fiber 132. The heat-shrinkable tubing also can serve as a protective layer or cover. This makes the fiber more robust and can improve NURD performance. Alternatively, plastic tubing may be slid over the fiber. This tubing outer diameter may also be cut in the form of a spiral to decouple longitudinal stiffness from rotational stiffness so as to improve NURD performance.

Figure 9:
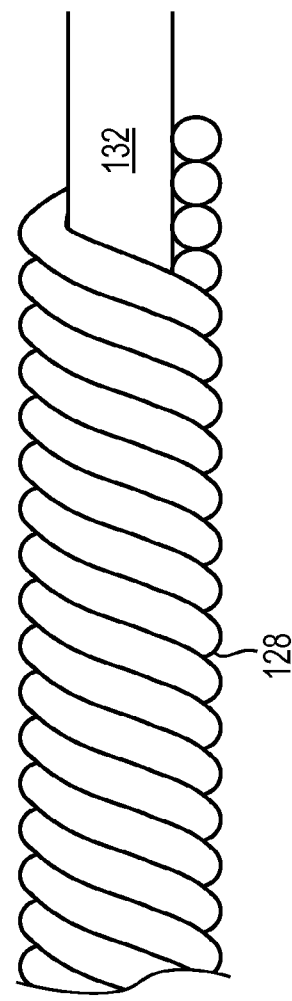
FIG. 9 is a side view of an embodiment of a torque wire.

In one embodiment, as shown in FIG. 9, there is an interference fit between the torque wire 128 and the optical fiber 132. In order to slide the torque wire 128 over the fiber 132, the torque wire 138 is held in a rotationally stressed open state to expand the inner diameter while the fiber is being inserted into the torque wire lumen. The stress is then released once the torque wire 128 has been positioned over the optical fiber 132. Alternatively, in one embodiment the torque wire 128 diameter is about 0.003" which gives an outer diameter of about 0.012" for this assembly when wound over a 125 µm fiber 132. The small size of the a catheter formed with a torque wire 128 formed over an optical fiber 132 over the entire length of the catheter allows the proximal section of the catheter to be smaller, making it easier to perform hand-powered flushes of the catheter lumen using a syringe to clear the blood from the imaging area. The interference fit between the torque wire and the optical fiber improves the mechanical stability of the combination and avoids the NURD issues associated with long, small-diameter torque wires.

Figure 10:
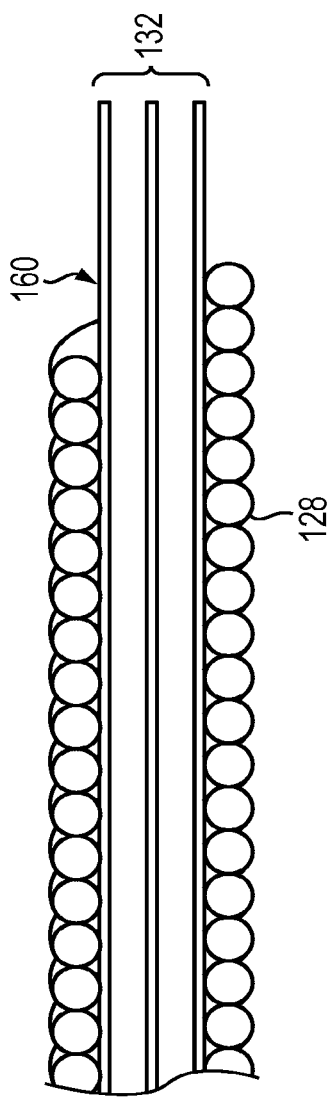
FIG. 10 is a longitudinal cross-section of the torque wire of FIG. 9.

In one embodiment (FIG. 10), a polyimide or acrylate buffer layer 160 is placed over the glass fiber 132 to limit access to air and thereby reduce hydrogen embrittlement of the glass. It also provides compliance between the optical fiber 132 and the torque wire 128, which helps the interference fit between them. The buffer layer 160 thickness may be varied to improve the NURD performance of the assembly.

Figure 11:
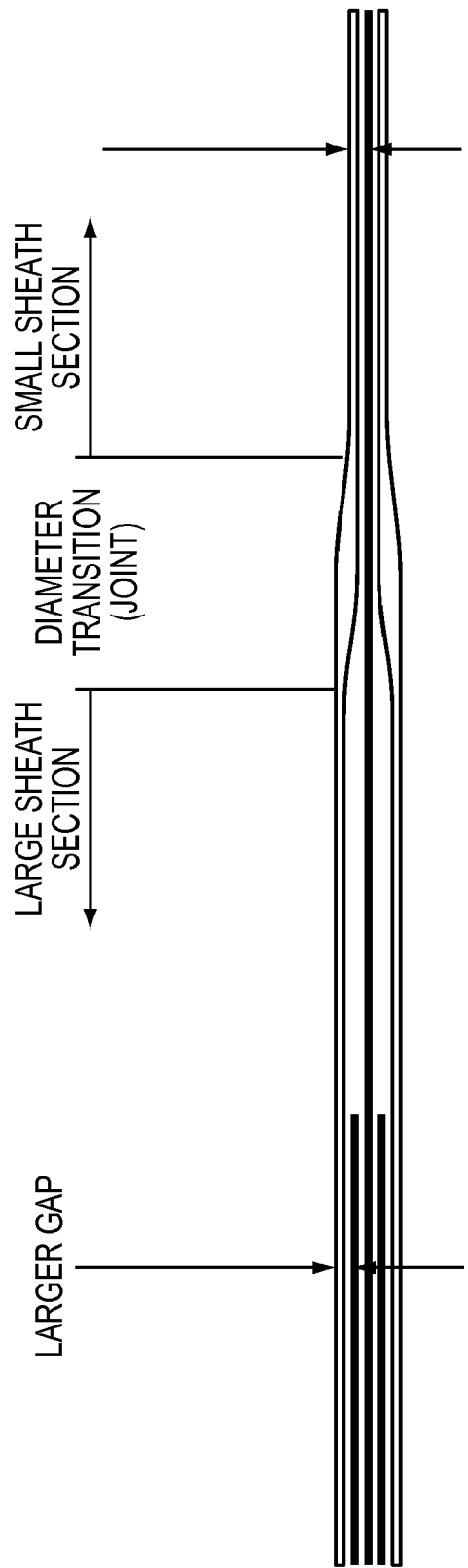
FIG. 11 is a longitudinal cross-section of an embodiment of a torque wire within a sheath.

For torque wire assemblies that have a step diameter change, the covering sheath will have a diameter step in it also. The diameter change in the sheath is shown in FIG. 11. The image core is shown fully advanced in the sheath. The image core may be withdrawn proximally to image a section of the target vessel without moving the sheath. There is no mechanical interference during withdrawal. The size of the gap between the sheath and the image core in the distal smaller diameter section is small. A small distal gap size reduces the lesion crossing profile and reduces the chance the distal sheath tubing can kink at small diameters.

Figure 12:
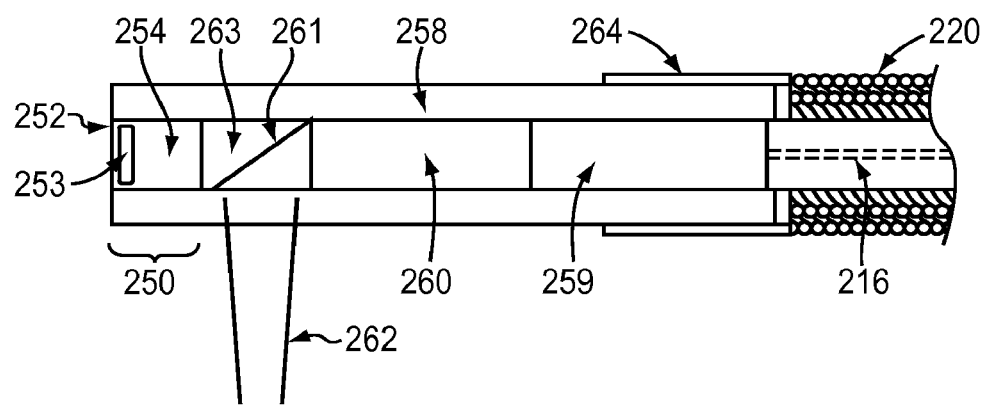
FIG. 12 is a schematic cross-sectional diagram of an embodiment of a pressure sensing OCT catheter.

Compared to the construction of the OCT optics, the pressure section of the probe is simpler. As shown in FIG. 12, an optical pressure transducer 250 may be used in conjunction with the OCT probe, both sharing the same fiber 216 for transmission of information. The optical pressure transducer 250 includes a diaphragm 252 and a transducer body 254, having a transducer air gap 253. The transducer 250 held on the optical train by a glass sheath 258. Light passing down a single mode fiber 216 is expanded by a coreless fiber portion 259 of the optical train and shaped by a multimode fiber portion 260 of the optical train. This light passes into an angle-cut coreless fiber prism 261 and is either reflected by the interface between the fiber prism 261 and the air gap 263 by total internal reflection or is passed through to the pressure transducer 250.

Light that is reflected by the interface with the air gap 263 is focused 262 out the side of the probe. Light at specific wavelengths that pass through the fiber prism 261 to the pressure transducer 250 is modulated by changes in the position of the diaphragm 252 relative to the transducer portion 254 and reflected back through the optical train and along the fiber 216. The modulation of the light is detected and converted to a pressure measurement. The pressure transducer can be configured as a Fabry-Perot cavity, such that pressure changes are detected as a modulation of the spectrum of the reflected light, or configured as a mirror whose reflectance at a specific wavelength depends on the applied pressure.

In one embodiment, the light used for pressure measurement lies within a different band of wavelengths from the light used in making the OCT images. The tip of the fiber is coated with a dichroic thin film and the wavelengths of the light used for pressure measurement are selected to allow the light to pass through the lens assembly of the optical train and the fiber prism 261 without deflection through the side of the fiber. Light from fiber 216 hitting the pressure transducer 250 is then reflected back down the optical train and fiber 216. As the pressure changes, the light is modulated and from the modulation the pressure can be calculated. In one embodiment, radio-opaque markers 264 mark the position of the lens assembly.

Figure 13:
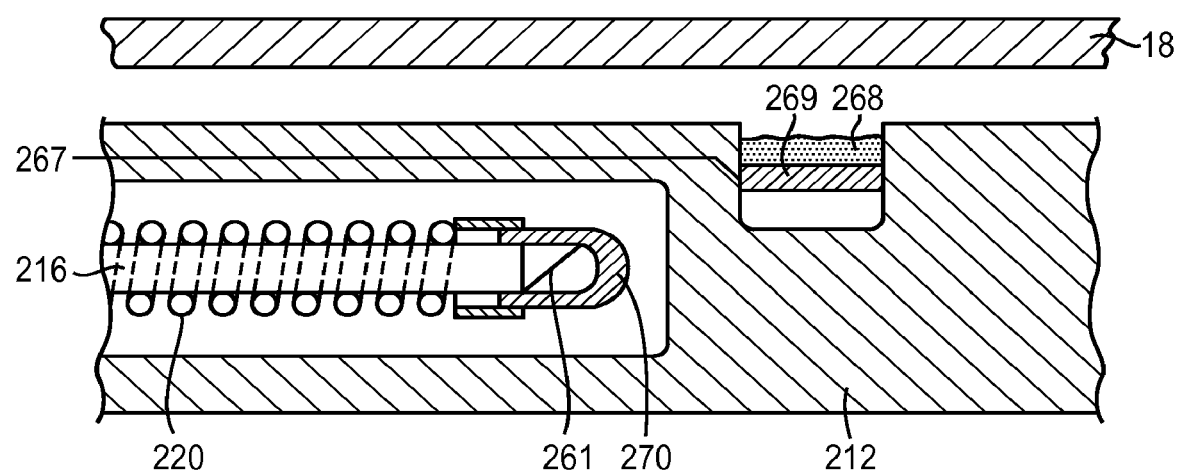
FIG. 13 is a schematic diagram of a cross-sectional of another embodiment of a pressure sensing OCT catheter.

An alternative combination pressure and OCT probe is shown in FIG. 13. As shown in FIG. 13, an electrical pressure transducer 269 is used to measure pressure. In contrast with FIG. 12, the transducer 269 is mounted in the sheath 212, not on the image fiber 216. There is no mechanical or optical connection between the fiber 216 and the pressure transducer 269. The wires 267 that run from the pressure transducer 269 to the proximal end of the catheter are co-extruded in the sheath wall 212. The sheath 212 defines an elongate cavity with one or more wires 267 disposed therein. The wire size is kept small to minimize the light blockage of the OCT fiber prism 261. In one embodiment, the pressure transducer 269 is held in a pocket in the sheath wall by a flexible silicone gel 268. In one embodiment, the optical train of the optical portion of the probe is held in place by a glass cap 270.

The electrical pressure transducer has an advantage over the optical pressure transducer in that the non-flexible section of the probe is shorter. With the optical pressure transducer, the glass sheath section 258 (FIG. 12) is not flexible. With the electrical pressure transducer only, the glass cap 270 is not flexible. A shorter non-flexible length allows the transducer to go into vessels with tighter radial bends.

Figure 14:
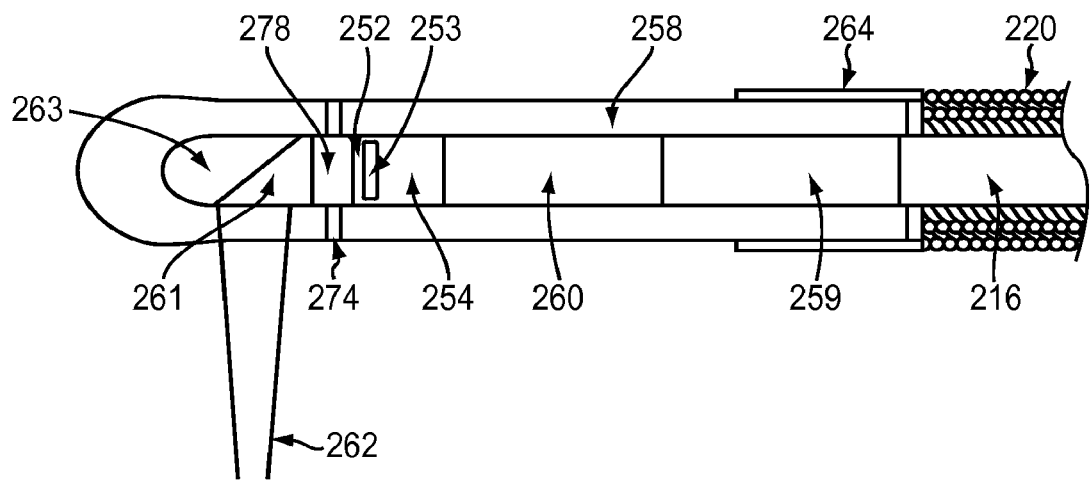
FIG. 14 is a longitudinal cross-section of an embodiment of a combination OCT/pressure probe.
Figure 15:
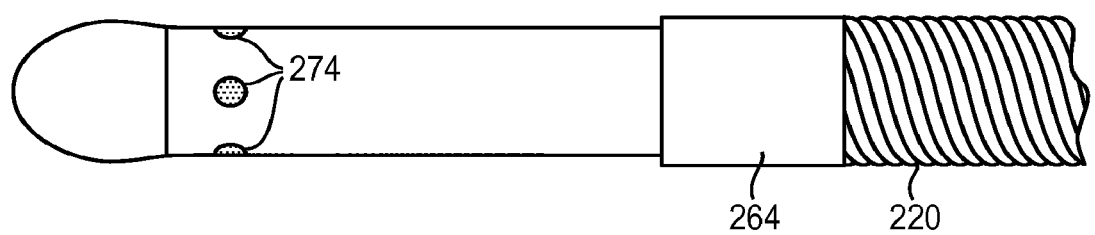
FIG. 15 is a side view of an embodiment of a combination OCT/pressure probe within a sheath.

FIG. 14 is yet another embodiment of an OCT pressure/ probe. In this embodiment, the pressure transducer 254 is located adjacent the beam shaper 260 portion of the optical train. Light passing from the single mode fiber 216 again passes through a beam expander 259, and the beam shaper 260 before passing through the transducer body 254. Adjacent to the diaphragm 252 of the transducer 254 is a region filled with a transparent gel 278. The gel is a low durometer silicone gel inserted between the pressure transducer diaphragm and the angle polished coreless fiber prism 261. Its purpose is to reduce the index mismatches between the angle polished coreless fiber prism and the pressure transducer diaphragm. This increases the light transmission. The gel is low enough durometer to accurately transmit pressure to the diaphragm and not interfere with the diaphragm's motion. The gel 278 is open to the environment of the probe through a series of pressure ports 274 (shown also in external side view in FIG. 15). Pressure applied to the port 274 is transmitted through the gel 278 to the diaphragm 252. As shown in FIG. 15, the torque wire 220 is next to a radio-opaque marker 264.

Light passing through the gel 278 enters the fiber prism 261 and is reflected by total internal reflection at the air gap 263 fiber prism 261 interface. The reflected beam 262 passes out through the side of the probe and impinges on the wall of the vessel. The light reflected by the wall passes in the reverse direction through the fiber prism 262, gel 278 and pressure transducer body 254 before being transmitted down the rest of the optical train. In this embodiment, the same band of optical wavelengths is used for OCT imaging and pressure sensing.

Figure 16:
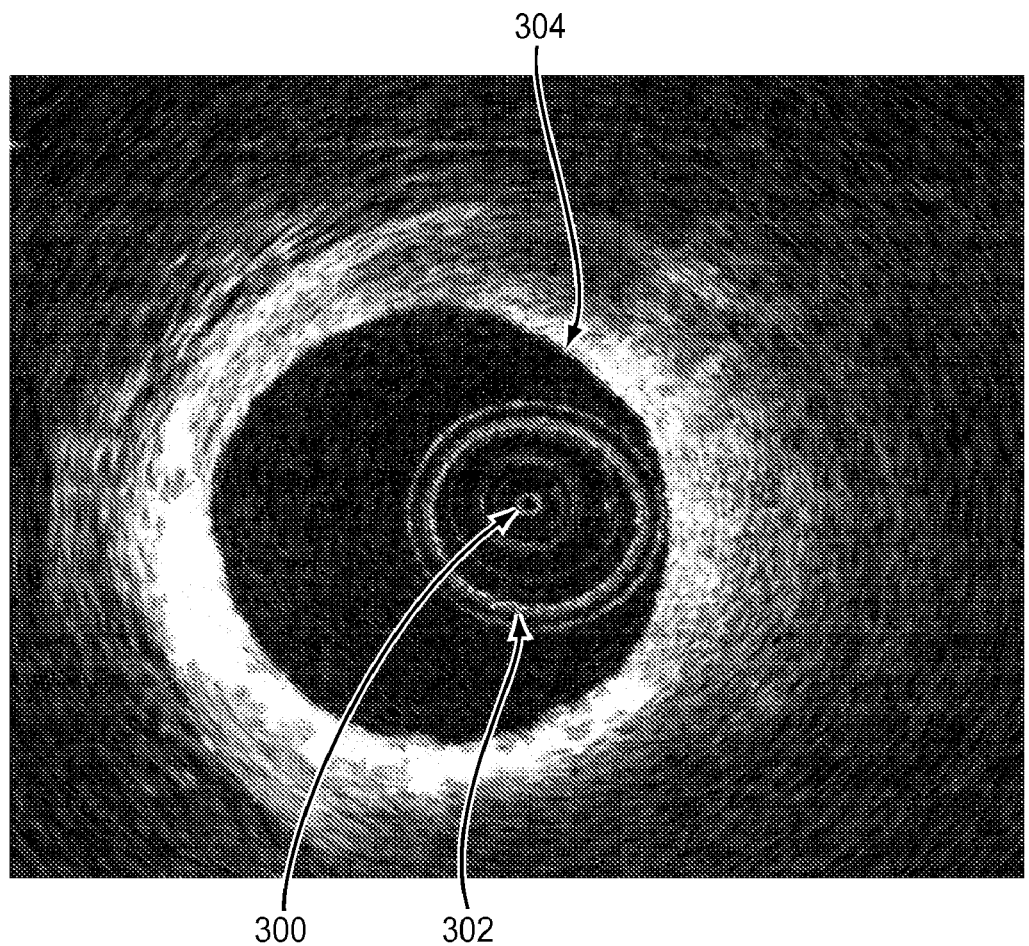
FIG. 16 is an image of a blood vessel wall taken with an OCT catheter.

The optical train including the pressure transducer appears as a circle 300 in the OCT image (FIG. 16) close to the center of the sheath 302. The probe is off axis with respect to the lumen wall 304. When the pressure transducer is in use (typically when the OCT probe is not rotating), pressure variations will cause the spectral interference pattern from the sensor to change which, in turn, will modulate the position of the circle 300 slightly, similar to what occurred in the embodiment of FIG. 12. The Fabry-Perot cavity spacing of the transducer is selected such that the position of the circle in the image does not interfere with the OCT image. The benefit of this embodiment is that the OCT data regarding the lumen can be measured at the same time the pressure data is being measured.

Figure 17:
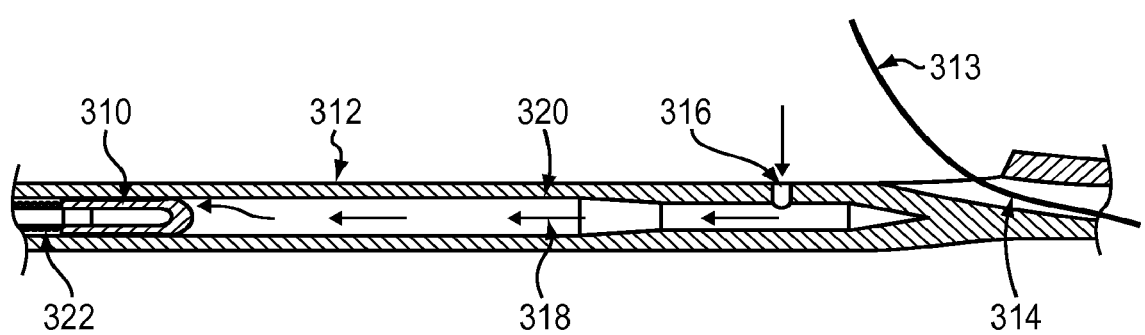
FIG. 17 is a schematic diagram of a cross-section of an embodiment of an OCT optical head in a catheter.

Referring to FIG. 17, the combination pressure and OCT probe 310 is placed in a catheter sheath 312 that has been inserted into a vessel over a guidewire 313 that is inserted first into the vessel. The sheath 312 is positioned in the vessel by threading the monorail tip of sheath 312 over the distal end of the guidewire 313 through the guidewire port 314. The fluid pressure exerted by the environment (arrows 318) is transmitted through a fluid port 316 into the fluid in the lumen 320 to the pressure port 322 of the probe 310 such as an OCT probe or a combination FFR/OCT probe.

In addition to making the FFR measurements before intervention, a combination IFR/OCT probe is also useful in determining whether a stent has been properly placed. With such a probe, OCT is used to check for stent underexpansion or misplacement and FFR is used to insure all significant stenoses have been removed.

Figure 18:
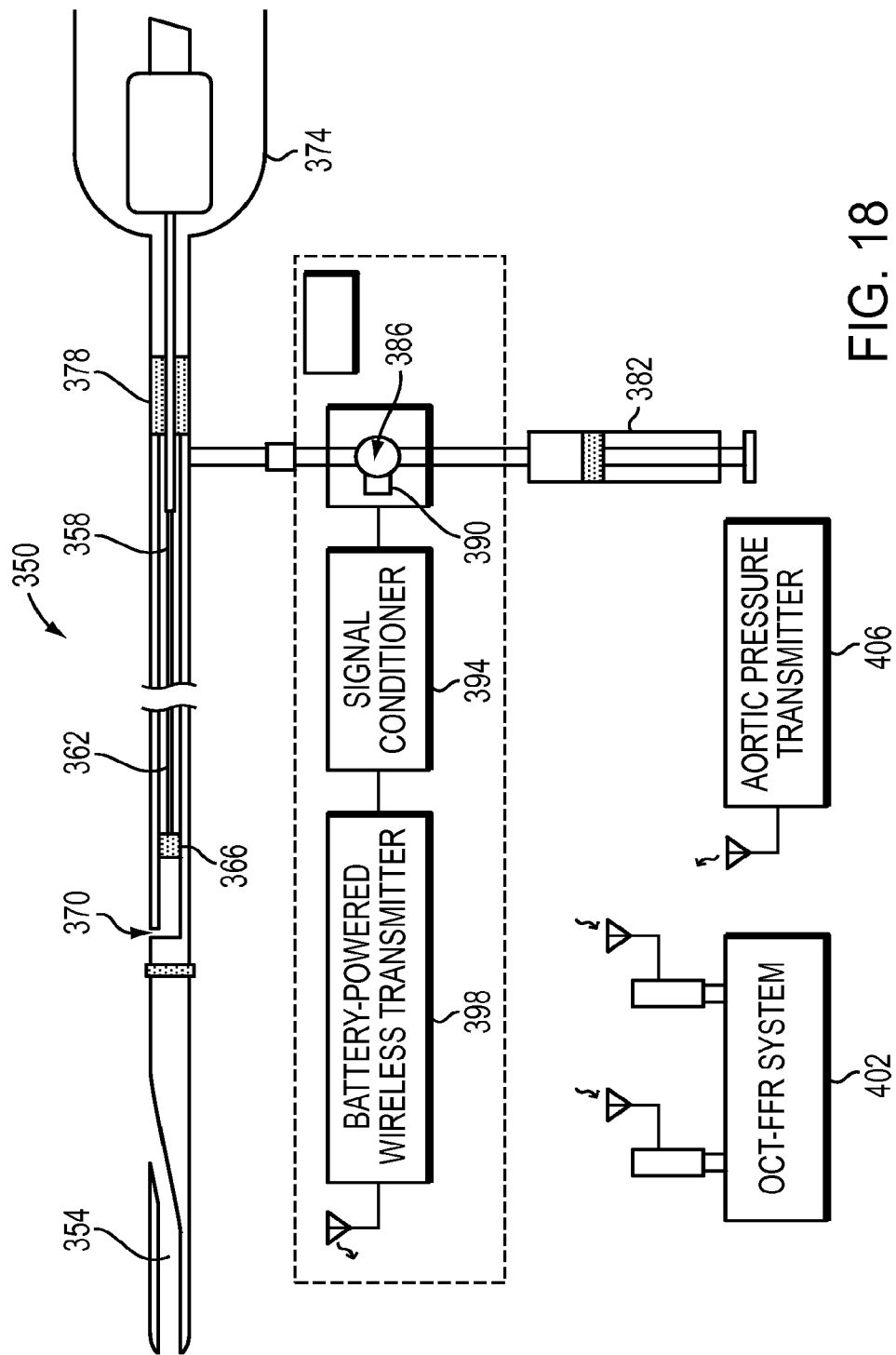
FIG. 18 is a block diagram of another embodiment of a pressure measuring system constructed in accordance with the invention.

FIG. 18 depicts an embodiment of a system used to measure vascular pressures accurately without the use of a transducer within the catheter. Such a system includes an OCT catheter 350 having a guidewire lumen 354 and a lumen 358 in which an optical probe 362 is located. The optical probe 362 includes an OCT lens 366 at its distal end and an optical connector 374 at the proximal end.

The lumen 358 is filled with a purge solution such as heparinized saline or other substantially incompressible fluid having an index of refraction that substantially matches the index of refraction of the OCT lens. The purge solution is configured such that it does not damp the transmitted pressure waves beyond an acceptable limit. This follows because if the pressure waves are excessively damped, it is harder distinguish if the catheter is not properly placed for pressure measurements. A liquid seal 378 keeps the fluid in the lumen 358 from leaking through to the fiber-optic connector 374. The lumen 358 includes a vent 370 through which the fluid flows to purge air from the lumen 358. The lumen 358 is connected to a fluid supply 382, in one embodiment a syringe, through a three way valve 386. In the first valve position, the fluid from the fluid supply 382 passes into the lumen 358. In a second valve position, the lumen 358 is connected to a pressure transducer 390. In one embodiment, the valve position is controlled automatically. In one embodiment, the fluid supply 382 is a syringe configured to dispense a purge solution such as water, saline, or other fluids and is in fluid communication with one or more fluid flow restricting or fluid flow controlling elements as shown in FIGS. 20-23 including a pressure transducer.

As shown in FIG. 18, the electrical output of the pressure transducer 390 is connected to a signal conditioning circuit 394 whose output, in one embodiment, is in turn is connected to a wireless transmitter 398. The wireless transmitter 398 is in communication with an OCT-FFR system transceiver 402. In another embodiment, the signal conditioner 394 is connected to the OCT-FFR system transceiver 402 by an electrical cable with a detachable connector. The OCT-FFR system transceiver is also able to communicate with an aortic pressure transmitter 406. In one embodiment, the pressure transducer 390 and conditioning assembly 394 are disposable and are supplied to user in sterile package already attached to purge syringe 382. In one embodiment, connection to the pressure transducer 390 is shut off during high-pressure purge of the lumen 358. In other embodiments, the pressure transducer 0390 can be used during one or more purge procedures, such as a continuous purge, a periodic purge, or a one-time purge.

When the lumen 358 is connected to the pressure transducer 390, through the valve 386 pressure is transmitted to the pressure transducer 390 through lumen 358 from the blood vessel environment through the purge port 370. The pressure waveform is expected to be damped by transmission of pressure through internal lumen 358 of OCT catheter. As long as the aortic and distal pressure wave shapes are similar, FFR measurement accuracy can be maintained. In a preferred implementation, an adaptive electronic digital filter can be used to maintain a suitable level of similarity between these two wave shapes. A circuit-based method or software is configured to shape the aortic pressure and/or the purge port pressure waveform. The digital filtering software function is intended to adjust the aortic and distal pressure wave shapes for best temporal correspondence. An example of a filter is a 1$^{st}$-order low-pass filter with a variable time constant that can be adjusted to match the normalized aortic and distal blood pressure waveforms to varying degrees of goodness of fit. Higher order filters with more than one adjustable parameter can also be used to compensate for the presence of microscopic air bubbles in the lumen that can introduce time constants of differing magnitude.

The two waveforms (aortic and distal pressure waveforms) can then be processed and displayed using time-synchronous methods similar to those employed in the current pressure measuring on FFR determining systems. Thus in operation, the clinician first sets the three port valve to a first position connecting the fluid reservoir to the lumen of the catheter that defines the purge port. Fluid from the fluid reservoir is then pumped through the lumen and out the purge port thereby purging the lumen of air. The clinician then places the catheter in the blood vessel of interest and moves the catheter into the vessel such that the purge port is positioned beyond the stenosis. Then by setting the three-port valve to a second position connecting the pressure transducer to the lumen of the catheter defining the purge port, the pressure in the lumen (and hence the pressure in the vessel itself, is measured using the pressure transducer 390.

Pressure-correction software calculates the excess pressure drop $\Delta P_{ex}$ caused by the larger cross section of the catheter compared to that of a standard pressure wire. According to the preferred implementation of the invention, the corrected value of the FFR is computed as $(P_d + \Delta P_{ex})/P_a$ where $P_d$ is the mean distal pressure measured at the purge exit port and Pa is the mean aortic pressure. $\Delta P_{ex}$ can be calculated analytically on the basis of the expected pressure drops derived from the OCT mean-diameter/area profiles of the lumen at a hyperemic flow estimated from the measured pressures and calculated resistances. Alternatively, for greater accuracy, a 3D computational flow (finite-element) model can be employed. Under most conditions, the excess pressure drop should be only a few mmHg, so precise $\Delta P_{ex}$ estimates should not be necessary.

Figure 19:
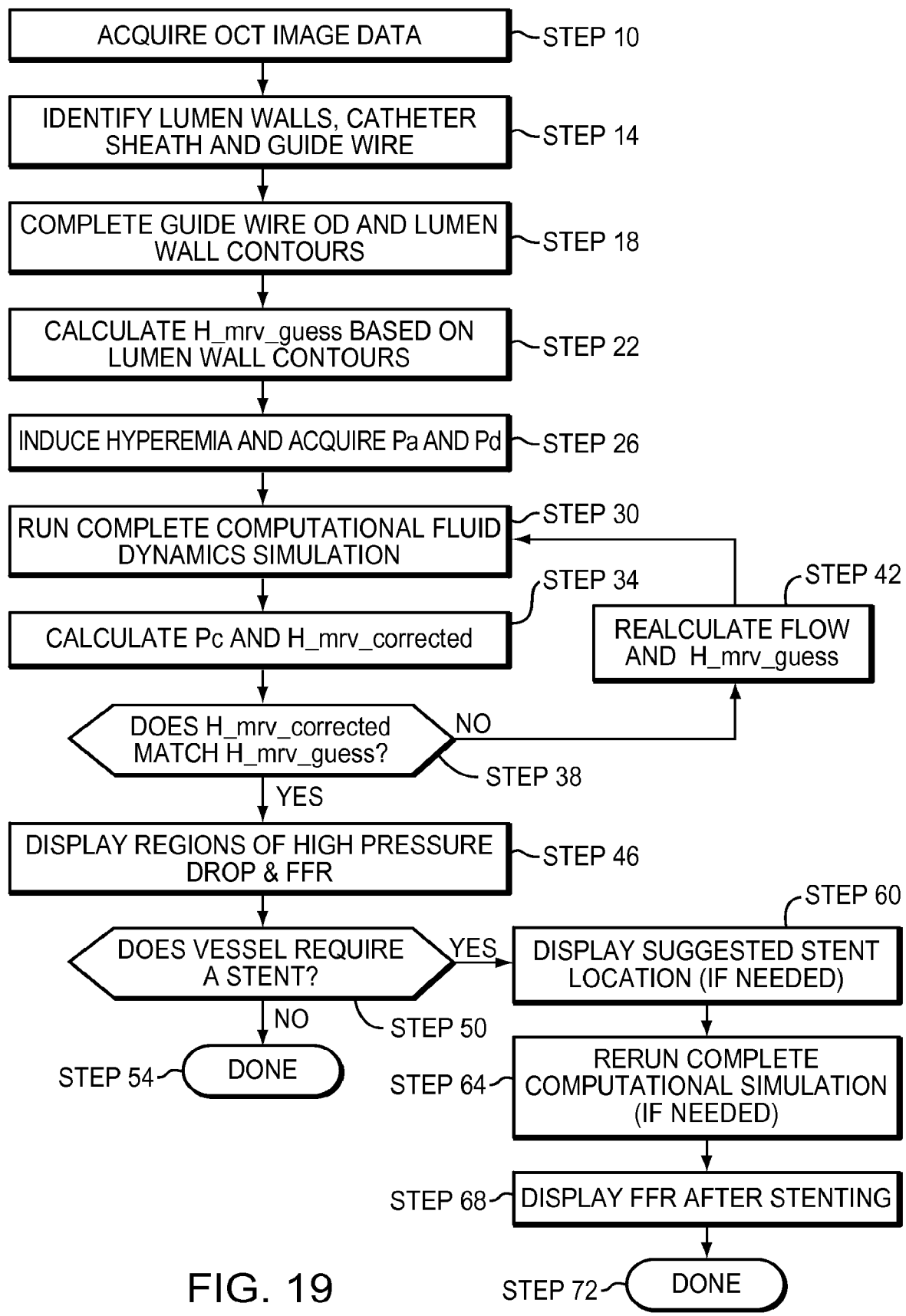
FIG. 19 is a flow diagram of an embodiment of a method for determining stent parameters according to an illustrative embodiment of the invention.

Referring to FIG. 19, the use of the system, including an OCT/pressure probe and a processor, to determine whether a stent should be introduced into a vessel is shown. The determination is begun by taking OCT image data (Step 10). From that image data, the lumen walls, catheter sheath and guidewire are identified (Step 14). The complete contours of the guidewire and lumen walls are determined (Step 18) and the value of H_mrv_guess based on the wall contours is calculated (Step 22).

Next, the patient is given adenosine to induce hyperemia and $P_a$ and $P_d$ are measured (Step 26). A fluid dynamic simulation is performed (Step 30) and $P_c$ and H_mrv_corrected are calculated (Step 34). The processor then determines if H_mrv_corrected equals H_mrv_guess to a predefined difference (Step 38). If values do not so agree, then the flow and H_mrv_guess are recalculated (Step 42) and the simulation (Step 30) rerun. This loop continues until H_mrv_corrected equals H_mrv_guess to a predefined difference. At that point the regions of high pressure drop and a calculation of FFR are displayed. From these measurements a determination if a stent is required is made (Step 50). If not, the procedure is complete (Step 54).

However, if a stent is required the system displays a suggested stent location (Step 60) and if needed another simulation is run to determine what the effect of the stent will be (Step 64). The stent is then placed in position. The FFR after stenting is then measured and displayed (Step 68) and the procedure completes (Step 72).

Pressure Measurements and Purging Assembly Embodiment

In part, the invention also relates to systems, methods and devices suitable for performing purging of a portion of a data collection probe having a purge port, such as a catheter, and performing a purge port pressure measurement. This type of measurement is discussed above with respect to FIG. 18. In one embodiment, the pressure at a position in the lumen of a vessel can be measured through a purge port disposed in the lumen by using a pressure measuring device in fluid communication with the purge port. Various types of fluid delivery or flow regulating systems or components can be used to perform purging and pressure measurements as shown in FIGS. 20-23. Some of these systems and components can be used with or in lieu of the system or components shown in FIG. 18.

Purging removes air from a catheter to prevent or reduce the amount of air bubbles being introduced in a blood vessel during a data collection procedure, such as image data collection, pressure data collection or when collecting other data of interest using a probe. The systems and/or components of FIGS. 20-23 can be used to purge an imaging catheter with a purge solution such as water or saline while preventing blood from flowing back into the catheter. A continuous drip of purge solution can help prevent blood ingress. In addition, the systems and components of FIGS. 20-23 can be configured to measure vascular pressures accurately without the use of a transducer within the data collection probe such as by having the transducer in-line with the purge solution supply.

In general, blood incursion prevention systems and flushing systems can be also implemented as described herein as part of a purge port pressure measurement system. Flushing can also be performed to clear blood from a vessel before it is imaged using a flush solution. In this way, flushing helps ensure that imaging artifacts and other unwanted effects due to blood incursion can be mitigated by clearing the blood field before image data is collected.

As described above, measuring pressure at different positions or points in time when collecting image data or other data in a vessel of interest offers advantages and additional information relative to the vessel of interest and the imaging probe being used. A pressure monitor such as a pressure transducer can be installed in various configurations as part of a purge system. This transducer facilitates obtaining FFR measurements and other measurements of interest that can be used alone or with OCT data collected with respect to the same vessel.

Figure 20:
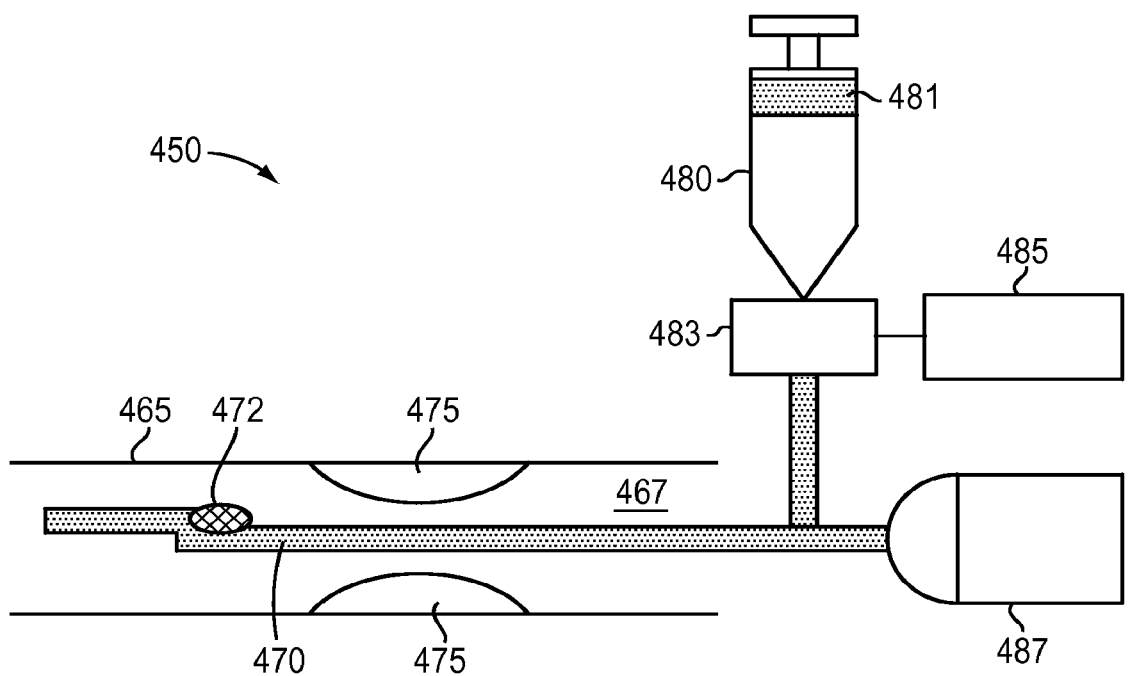
FIG. 20 is a schematic diagram of a data collection system that includes a purging device and a pressuring monitoring device according to an illustrative embodiment of the invention.

FIG. 20 is a schematic diagram of a data collection system 450 suitable for use with a vessel of interest 465 such as an artery or other blood vessel having a lumen 467. A data collection probe 470 such as OCT probe that includes a catheter and/or one or more elongate sheaths with an image data collecting element disposed therein can be disposed in the lumen 467 of the vessel 465. The probe 470 can include a catheter with a rotatable optical fiber disposed therein. The probe 470 can also include or be in communication with a pressure data collecting element. As shown, the probe 470 can be advanced past and used to collect image data with respect to a narrowing of the vessel 475 such as caused by a stenotic lesion. Pressure data can likewise be collected at different points in time and at different positions in the vessel such as on either side of the narrowed region 475. In one embodiment, the rotatable optical fiber component disposed within the catheter can be pulled through the lumen 467. The probe 470 can be an OCT probe or a multimodal data collection probe. The probe 470 can also include a purge port 472.

The system of FIG. 20 includes a fluid supply 480 such as a syringe which may contain a purge solution alone or also include air 481. The fluid supply 480 is in-line with a pressure transducer 483. Thus, purge solution passes around or through the pressure transducer 0483 in one embodiment. Flow rate changes and pressure changes can cause unwanted oscillations or damping with respect to pressure readings obtained using transducer 483; however, this can be mitigated as outlined herein. In turn, the pressure transducer 483 is in electrical communication with a wireless or wired transmitter 485. The transmitter is configured to transmit data obtained using the transducer 483. A fiber optic connector 487 is also shown in communication with the probe 470. The fiber optic connector 487 can be attached to the patient interface unit (PIU). In one embodiment, the fiber optic connector 487 is rotatable and is in communication with a motor configured to rotate an optical fiber disposed in a data collection probe. The probe 470 typically includes a rotatable optical fiber; however, it can include a forward scanning probe or other probe types. Various fluid pathways such as conduits, connectors, channels, etc. can be used to deliver a flush solution from the fluid supply 480 through the various elements shown in FIGS. 20-22 to the catheter or probe 470 shown.

Figure 21:
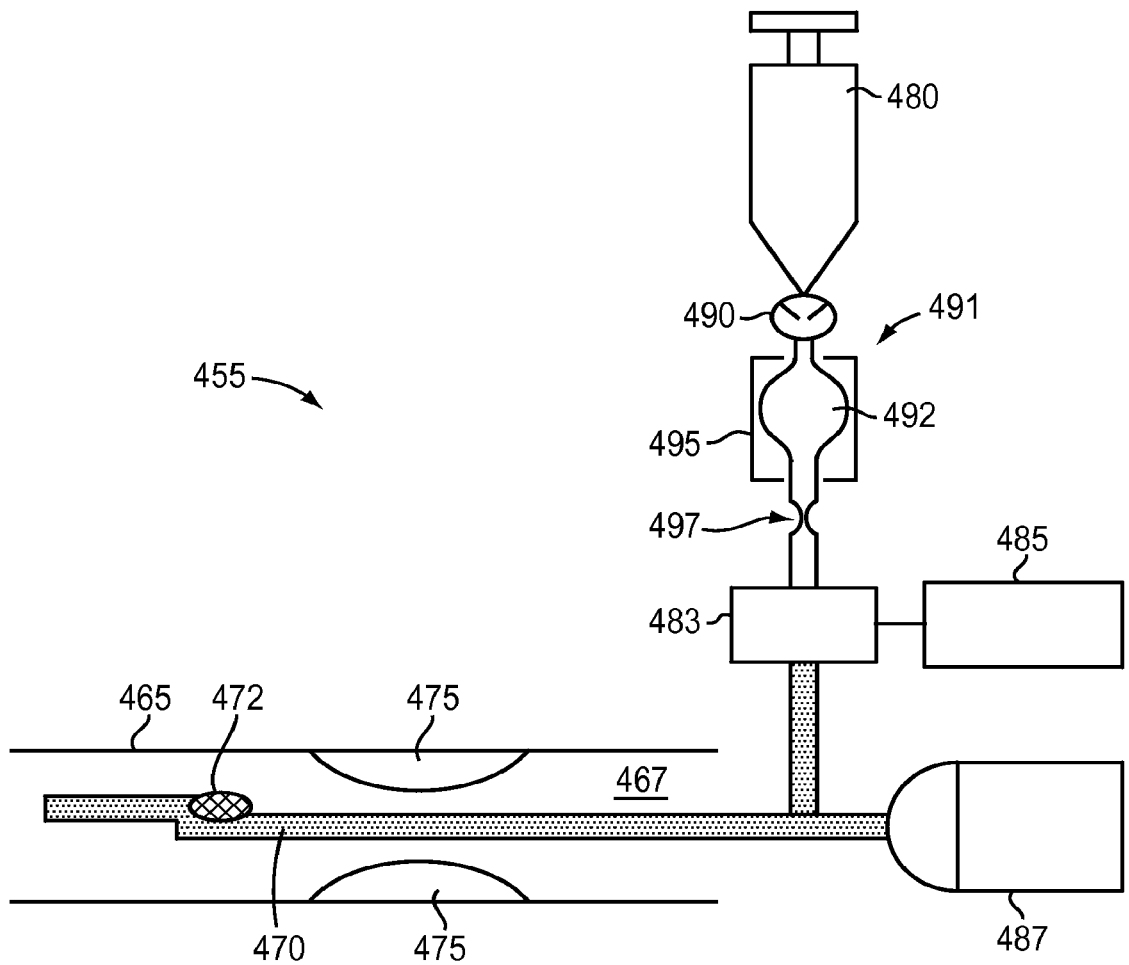
FIG. 21 is a schematic diagram of a data collection system that includes a purging device, a fluid flow control device and a pressuring monitoring device according to an illustrative embodiment of the invention.
Figure 22:
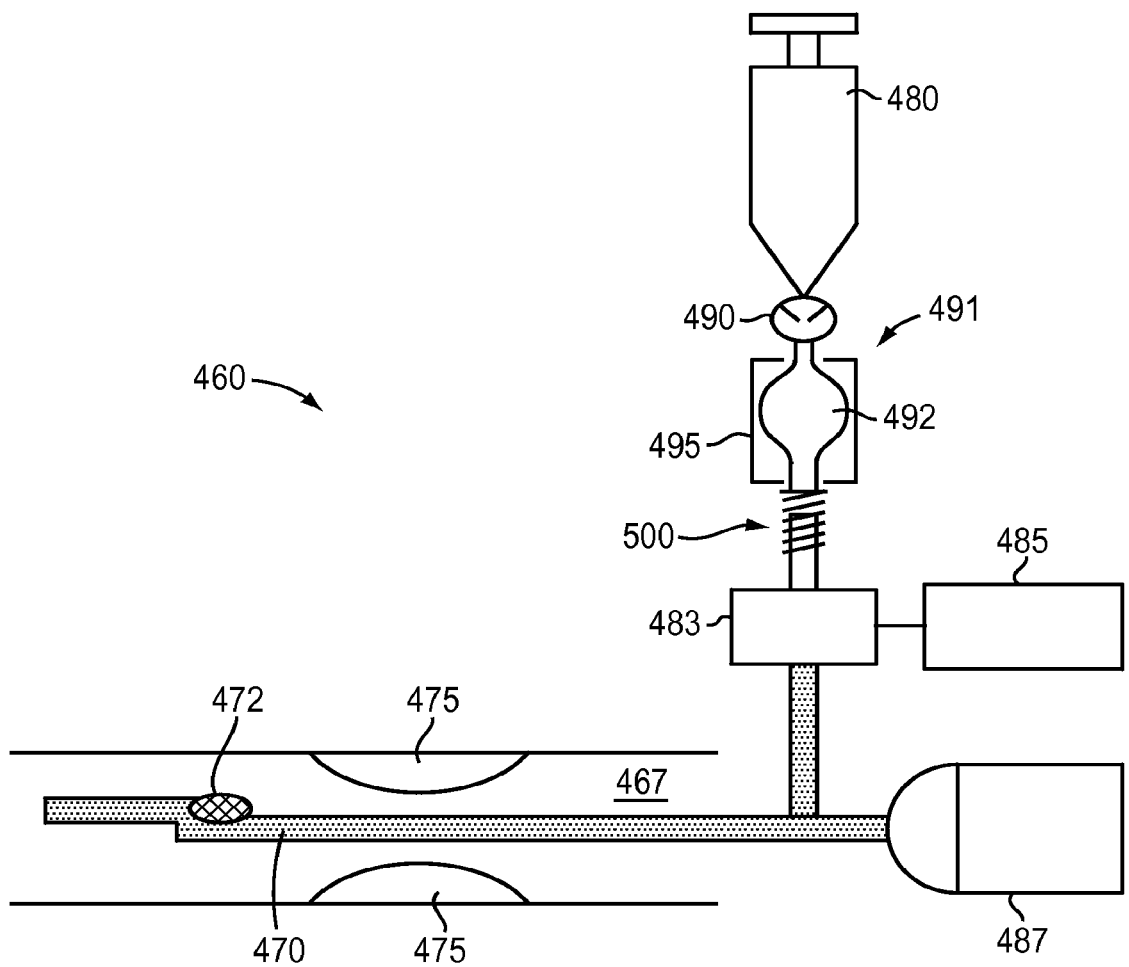
FIG. 22 is a schematic diagram of a data collection system that includes a purging device, an adjustable fluid control device and a pressuring monitoring device according to an illustrative embodiment of the invention.

With the configuration shown in FIG. 20, the amount of air 481 in the syringe can change the damping level of the pressure waveform and thus can vary the average pressure readings. The amount of liquid in the syringe can also affect the pressure readings when air 481 is present. One approach to solving some of these damping related challenges is to add additional purge fluid controlling elements as shown in FIGS. 21 and 22. These features help stabilize pressure readings obtained using the transducer 483. The system 450 of FIG. 20 has the advantage that the procedure of operating an OCT system remains unchanged or substantially unchanged.

FIG. 21 is a schematic diagram of a probe system 455 suitable for use with a vessel of interest 465 such as an artery or other blood vessel having a lumen 467. The system 455 includes a fluid supply 480 such as a syringe that is in fluid communication with a check valve 490 and a fluid flow control device 491. The check valve 490 is configured to keep liquid from flowing back into the fluid supply 480. In one embodiment, the check valve 490 contains a three way valve to facilitate filling the syringe and purging air.

In one embodiment, the fluid control device 491 includes an expandable tube 492 disposed in an expansion limiter or housing 495. The expandable tube 482 can expand radially and longitudinally in some embodiments such that one or both ends can move as tube elongates. The expansion limiter 495 can include another tube, a collar, a volume restricting chamber, or other expansion limiting element. The fluid flow control device 491 can include an expandable tube 492 that is disposed in another restricting tube or collar 495. A fluid flow restricting device or restriction 497 is also in fluid communication with the device 491 as shown.

The restriction or restricting device 497 shown can include a crimp or narrowing formed in a tube or other channel in fluid communication with fluid flow control device 491. The restriction or restricting device 497 is not adjustable in one embodiment and can be an optional design element in one embodiment. In one embodiment, the restriction or restricting device 497 is in fluid communication with the fluid control device 491, such as with tube 492 in embodiments having such a tube 492, and the pressure transducer 483 as shown. The transmitter 485 transmits data received from the pressure transducer 483 as shown. The transmitted data can include pressure measurements or data from which pressure measurements can be derived.

In operation, fluid expelled from the supply 480 is selectively passed or restricted by valve 490 prior to entering fluid flow control device 491. As fluid from supply 480 enters the flow control device 491, in one embodiment, an expandable tube 492 expands to accommodate the entering fluid until the expansion limiter 495 constrains the fluid containing and expanded tube 492. In one embodiment, the fluid flow control device 491 can include an expandable device that expands from a first state having a first volume, such as for example when no fluid is applied from supply 480 or when fluid is in the tube 492 without substantially expanding it. The expandable device, which can include tube 492 or other expandable element, can expand to a second state having a second volume, such as when the tube 492 is fully expanded and constrained from further expansion by expansion limiter 495. The length, width and height of the tube can change as it expands in one embodiment.

Once the fluid flow control device 491 is filled with a bolus of purge solution from supply 480 and additional purge solution is not delivered from the supply 480, the expandable element such as the tube 492 applies force on the purge solution disposed therein as the expanded element, such as tube 492, returns to its unexpanded state. In this way, the bolus of purge solution is driven from the fluid flow control device 491 into the restriction or restricting element 492. The pressure of the fluid departing the restriction or restricting device 497 can be measured using pressure transducer 483, which is in fluid communication and/or in-line with the restriction or restricting device 497. Similarly, back pressure from a purge port 472 can also be measured using the transducer 483. The purge solution passing through the fluid transducer 483 continues on into the sheath of the probe 470 where it is expelled through a purge port 472 into lumen 467 or into the atmosphere if it is purged outside of the body. In one embodiment, when the purge port 472 is in fluid communication with the pressure transducer 483, pressure is transmitted to the pressure transducer 483 from the lumen 467 that can be measured and used to determine one or more FFR values or other pressure-based parameters of interest. These FFR values can include corrected FFR values or FFR values obtained at different points in time with the same or different probes.

In one embodiment, the invention relates to a method of operating a purge system that includes a pressure transducer in fluid communication with a purge solution supply. The method can include the steps of opening a three way valve attached to the check valve 490, purging the catheter or probe, and closing the check valve. In one embodiment, the check valve 490 is passive such that it opens and closes without a user actively opening or closing it such as with a lever. Additional steps can include determining a FFR measurement using OCT data and/or pressure data obtained from transducer 483. In addition, once the FFR measurement has been determined, additional steps that include collecting image data such as by performing an OCT pull back can be performed. The system of FIG. 21 is suitable for performing one or more of the method steps described herein. This type of system eliminates compliance issues associated with the fluid supply 480. In addition, in some embodiments, a continuous or substantially continuous purge is performed, which maintains the probe 470 in a sufficiently blood cleared state during image data collection. The bolus of purge solution which forms in device 491 is suitable for maintaining a continuous purge.

In one embodiment, the degree to which the expandable tube 492 or other expandable element disposed in device 491 is full is monitored. The monitoring can be performed using transducer 482 or a cuff or other element in communication with device 491 or a component thereof. In embodiments in which the expandable tube 492 or the element has a sufficiently large capacity and/or a fluid flow or drip rate from the device 491 is slow enough, monitoring of tube expansion or fullness is optional and often not necessary.

In one embodiment, the operation of the system of FIG. 21 occurs as a sequence of steps. Initially, the fluid supply 480 is compressed, such as by a plunger. In turn, when the pressure generated by the fluid supply 480 exceeds an expansion pressure of the expandable tube 492, then the tube 492 will expand until its outer diameter presses against the expansion limiting element 495. Thus, if the expansion limiter is a tubular member having an inner diameter, the inner diameter of the expansion limiter confines the expansion of the expandable tube 492. The length of the tube 492 can also expand and if one end of the tube 492 is fixed the other end can expand and contract along its length.

With respect to purge fluid exiting the tube 492, such purge fluid will flow through the restriction or restricting device 497 and into the probe or catheter 470. In one embodiment, a restriction 497, such as a narrowing in a fluid flow channel, is used to control the flow of the purge liquid from the probe 470. Once the purge fluid is in the probe 470, it is expelled into the vessel 467 during the purge period. In FIG. 21, a discrete restriction 497 is positioned between the pressure transducer 483 and fluid supply 480 to help stabilize pressure measurements as a result of the transducer 483 receiving varying fluid flow and pressure waves from supply 480 or device 497. Alternatively, the restriction can be along the length of a sheath, such as a catheter, which is part of the probe 470 by configuring a gap between the optical fiber disposed in the probe 470 and the sheath inner diameter (ID) to be sized to constrain the flow of purge solution as is the case when a restriction 497 is used. This type of gap sizing to achieve restriction in a probe embodiment limits the purge solution flow; however the distance between the outer diameter of the fiber and the inner diameter of the sheath needs to be set such that transmission of pressure is still measurable using a transducer.

In one embodiment, the expandable tube 492 is configured to enlarge in response to an applied pressure, such as a first or opening pressure threshold, and contract or close when the applied pressure drops below that threshold value. The pressure to expand the tube 492 can be set equal to a pressure that can be generated by the fluid supply 480 such as for example the maximum pressure that can be generated by a syringe serving as the fluid supply 480. If the fluid supply is a 10 ml syringe, for example, the maximum pressure is about 150 psi in one embodiment. The applied pressure that causes the tube 492 to expand is proportional to the wall thickness of the tube multiplied by the modulus of elasticity of the tube 492 divided by the inner diameter of the tube 492. For a given tube 492 of a particular material, evaluating the change of the modulus of elasticity curve for the tube 492 relative to the strain level can be used to determine the proportionality constant to relate the applied pressure to the other measured values of the tube 492 discussed above.

In one embodiment, the expandable tube 492 includes a material that maintains its elasticity when subjected to strains such as those caused by pressure from supply 480. One suitable material for forming the expandable tube is Tecoflex 80 (available from The Lubrizol Corporation Wickliffe, Ohio). A tube of inner diameter of about 0.12 inches that has a wall thickness of about 0.02 inches is suitable for use with embodiments of the invention; however, other tube geometries and shapes can be used without limitation.

The expansion limiter 495 prevents the expandable tube 492 from over expanding and provides rigidity to the tube 492 in one embodiment. The expansion limiter 495 can be attached to the expandable tube 492 at both ends. The length of the expandable tube 492 is selected to give the correct volume for a given type of purge and for user convenience. In one embodiment, the length of the expandable tube is about 25 cm; however, in other embodiments the length of the expandable tube can range from about 1 cm to about 80 cm (or longer).

In FIG. 22, a system 460 including elements or subsystems that has some components in common with the system of FIG. 21 and one or more additional components is shown. Specifically, system 460 replaces the fixed restriction 497 with an adjustable restriction such as an adjustable fluid restricting element 500. Additional details relating to an exemplary adjustable restriction element 501 are described below with respect to FIG. 23. The installation of an adjustable fluid restricting element 500 has several benefits as shown in FIG. 22. These include a simplified purge operation when using a data collection probe 470. The embodiment of system 460 does not cause any significant effects with respect to the pressure readings varying or excessive damping. In addition, a purge system with an adjustable restriction 500, 501 can be configured to deliver a continuous purge that will prevent blood ingress into the imaging area such that image data can be collected.

With respect to the system 460 of FIG. 22, when a purge is initiated, the purge solution causes the expandable tube 492 to move and contact the expansion limiter 495 that surrounds the tube. In turn, this movement of the expandable tube 492 causes the adjustable restriction device 500 to open in response to fluid pressure in the tube 492. Similarly, when the initial purge is complete caused by depressing the plunger, the adjustable fluid restricting element 500 closes in response to the pressure of the fluid in tube 492 dropping below the threshold required to open the adjustable fluid restricting element 500. The use of an adjustable fluid restricting element such as device 500, 501 and/or components thereof facilitates consistent performance during a purge. The systems of FIGS. 20-22 are self-deairing. That is, the liquid flow from the supply 480 removes the air in the flow path. A separate deairing step is not needed.

Figure 23:
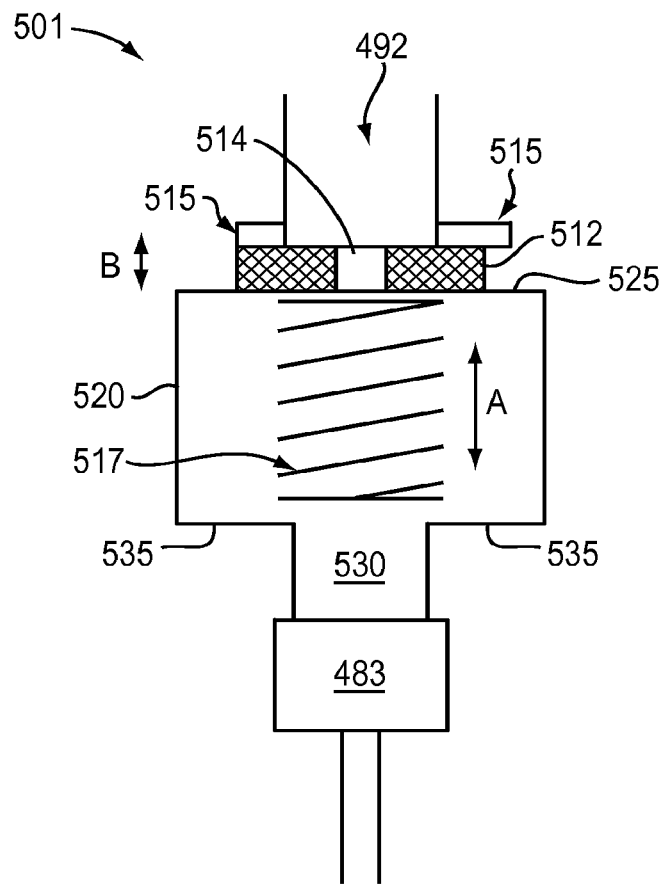
FIG. 23 is a schematic diagram of an adjustable fluid control device according to an illustrative embodiment of the invention.

FIG. 23 is a schematic diagram of an adjustable fluid control device 501 such as can be used with the system of FIG. 22 or other image data collection systems. In FIG. 22, device 500 can include device 501 or be used in lieu of that one or more components of device 501. Alternatively, another adjustable fluid control or restriction device can be used for device 500. The adjustable devices 501, 500 can be configured such that an initial or first bolus or release of purge solution is directed to the probe 470 and subsequently expelled from the purge port 472 and then a second more continuous release of purge solution occurs in response to a reduced applied pressure. The second release of purge solution can be a continuous flow of purge solution. These devices 501, 500 are configured to have a consistent operation with reduced variations in pressure measurements. The adjustable fluid control device 501 can be in fluid communication with tube 492 or more generally with device 491 and a pressure transducer 483.

As shown, the adjustable restriction or fluid control device 501 can be in fluid communication with a pressure transducer or other pressure detecting device 483. The device 501 can include a slidable member or plug 512 that defines a hole or bore 514. The plug or slidable member can be formed any suitable substrate and can be shaped formed as a disk, washer, or other annular or other hole or cavity defining member. The hole 514 can be a cylindrical cavity or other cavity defined by the plug 512. The hole is disposed relative to a sealing seat 515. Further, the slidable member or plug 512, such as a washer or disk that defines the hole 514 is held against the seat 515 by a biasing or compressible element 517 such as a spring. The hole 414 may also be made in the body of the device 520 or between the body 520 and the plug 512. It does not need to be wholly incorporated in the plug 512. It simply communicates fluid between 492 and 530 in a restricted manner.

In one embodiment, the seat 515 includes a boundary in contact with device 491 such as through tube 492 as shown. The seat 515 can be configured to abut slidable member 0512 when the member is biased against the seat 515 as a result of the application of force from the biasing element 517. The seat 515 can be configured to form a fluid tight seal with the slidable member 512 which in turn can form a fluid tight seal with surface 525 such that fluid will only flow through hole 514 and subsequently through channel 530 under certain purging scenarios.

The device 501 includes a housing 520 sized to contain the biasing or compressible element 517 and receive slidable member or plug 512 when element 517 is sufficiently compressed. The housing 520 at least partially defines a volume that includes the element 517 and allows it to move within the volume in response to the application of force such as along the A directions. The housing has different sides having surfaces such as a top surface 525 to receive the slidable member 512, which is configured to move along one or more directions such as the B directions. These directions A and B are typically the same, but are shown to indicate that element 517 and slidable member 512 can both move. The device 501 also has one or more internal fluid flow paths configured to allow purge solution to exit through channel 530 and flow in line with pressure transducer 483. In one embodiment, when biasing element 517 is compressed purge solution from a supply, such as a syringe, can flow through channel 530. In one embodiment, the pressure resulting from fluid flowing from tube 492 or device 491 is sufficient to cause slidable member or plug 512 to move within the volume defined by the housing 520 and approach the bottom wall 535. For example, during operation in one embodiment, seat 515 contacts the surface 525 and the plug 512 is driven toward wall 535 by a bolus of purge solution entering from tube 492 before flowing through channel 530.

During operation, when a spring 517 is used as the biasing element, when the syringe containing the purge solution is subjected to a sufficient level of compression, the expandable tube 492 will expand as a result of the incoming purge solution. When the expansion is sufficiently large enough, the pressure inside the tube 492 is high enough that the pressure on the slidable member 512 compresses the spring 517, opening the adjustable restriction 501. In one embodiment, the length of the tube 492 expands and moves against the plug 512 causing it to move into the chamber defined by housing 520. Additional fluid constraining walls and housings not shown can be disposed around housing 520 and seat 515 as suitable to properly contain and direct purge solution to a purge port.

In one embodiment, when the purge is complete, an operator releases the pressure from the syringe and the plug 512 is again pressed against the seat 515. When the plug 512 abuts the seat 515, purge solution only flows from the hole 514. The hole 514 can be made small enough to provide a slow purge flow to keep the imaging area clear. The flow is configured to be slow enough so as not to cause the pressure readings to vary excessively. Choices with respect to the spring constant of element 517, the size of the plug 512 and the dimensions of the hole 514 and the other dimensions and sizes of the housing 520 and device 501 allow flexibility when tailoring the adjustability of element 501 relative to the objectives of a given purge and the desired flow rate of a purge solution.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

Non-limiting Software Embodiments for Pressure Monitoring and Related Features

The present invention may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present invention, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating OCT data, OCT images, vascular resistance, FFR calculation, pressure sensing, contour detection and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, interferometer signal data, pressure calculation, interpolation, formulas, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

While the present invention has been described in terms of certain exemplary preferred embodiments, it will be readily understood and appreciated by one of ordinary skill in the art that it is not so limited, and that many additions, deletions and modifications to the preferred embodiments may be made within the scope of the invention as hereinafter claimed. Accordingly, the scope of the invention is limited only by the scope of the appended claims.

The invention claimed is:

1. A method of determining one or more intravascular parameters of a blood vessel comprising:
   receiving, at one or more processors from an intravascular probe, intravascular image data relating to the blood vessel;
   determining, based on the intravascular image data, a first geometric boundary of a first portion of a lumen of the vessel;
   determining, based on the intravascular image data and the first geometric boundary, a second geometric boundary of a second portion of the lumen of the vessel different from the first portion, the second portion of the lumen being located behind a guidewire disposed within the lumen;
   determining, based on the first geometric boundary and the second geometric boundary, a third geometric boundary of the guidewire, the third geometric boundary being located within the first geometric boundary and the second geometric boundary;
   measuring, using a pressure measuring device disposed within the intravascular probe, one or more pressure values at one or more predetermined locations in the vessel;
   determining, using the one or more processors based on the one or more pressure values, a first fractional flow reserve of the vessel;
   iteratively correcting a hyperemic microvascular resistance index until a predefined error limit is reached, wherein the hyperemic microvascular resistance index is determined using a calculated pressure drop value and the one or more pressure values, wherein the predefined error limit relates to the difference between the calculated pressure drop and the difference between the one or more pressure values;
   calculating, based on the one or more pressure values and the corrected hyperemic microvascular resistance value, an estimated pressure drop associated with removal of the third geometric boundary from the vessel;
   calculating, using the one or more processors based on the estimated pressure drop, a first corrected fractional flow reserve; and
   displaying the first corrected fractional flow reserve.

2. The method of claim 1, wherein the step of determining the geometric boundary of the second portion of the lumen closes a perimeter of the lumen.

3. The method of claim 1, wherein the pressure measuring device is a pressure transducer in fluid communication with a purge port of the first intravascular probe in the vessel and wherein the pressure value is measured at a predetermined location near the purge port.

4. The method of claim 1, further comprising determining the first fractional flow reserve by dividing a first pressure measured distal to a stenosis by a second pressure measured in an ostium.

5. The method of claim 4, wherein the processor further calculates the first corrected fractional flow reserve by correcting the first fractional flow reserve using three dimensional hydrodynamic equations, including the microvascular resistance index, and the first geometric boundary the second geometric boundary.

6. The method of claim 1, further comprising:
   determining, using the processor, a second fractional flow reserve in the vessel;
   correcting, using the processor, errors introduced by an obstruction in the vessel to determine a second corrected fractional flow reserve; and
   comparing the first corrected fractional flow reserve and the second corrected fractional flow reserve.

7. The method of claim 6, wherein the obstruction is the first intravascular probe, a second intravascular probe, a stenosis, a guidewire, or a stent.

8. The method of claim 6, further comprising outputting a damage index in response to the step of comparing.

9. A method of determining one or more intravascular parameters of a blood vessel comprising:
   optically measuring one or more pressure drops at one or more predetermined locations in the vessel;
   determining, using intravascular image data of the vessel, a first geometric boundary of a first section of the vessel;
   determining, based on the intravascular image data and the first geometric boundary, a second geometric boundary of a second portion of the lumen of the vessel different from the first portion, the second portion of the lumen being located behind a guidewire disposed within the blood vessel;
   determining, based on the first geometric boundary and the second geometric boundary, a third geometric boundary of the guidewire, the third geometric boundary being located within the first geometric boundary and the second geometric boundary;
   determining a mean area or a mean diameter profile for the section of the vessel using the geometric boundary;
   determining one or more expected pressure drops using the mean area or mean diameter profile, wherein the determining includes iteratively correcting a hyperemic microvascular resistance index until a predefined error limit is reached, wherein the hyperemic microvascular resistance index is determined using a calculated pressure drop value;
   determining a corrected fractional flow reserve value based on the hyperemic microvascular resistance index; and
   displaying the corrected fractional flow reserve value using an optical coherence tomography system.

10. The method of claim 9, further comprising displaying the hyperemic microvascular resistance index.

11. The method of claim 9, further comprising determining an initial fractional flow reserve by dividing a first pressure measured distal to a stenosis by a second pressure measured in an ostium.

12. The method of claim 9, wherein optically measuring the plurality of pressure values is performed distally relative to wherein the intravascular image data is obtained.

13. The method of claim 9, wherein the corrected fractional flow reserve values is iteratively obtained such that one or more corrections are made to reduce errors associated with optical imaging and optical pressure sensing measurements.

14. A system comprising:
   an intravascular probe disposed within a blood vessel;
   a pressure measuring device;
   one or more processors, the one or more processors configured to:
     receive, from the intravascular probe, intravascular image data relating to the blood vessel;
     determine a first geometric boundary of a first portion of a lumen of the vessel;
     determine, based on the intravascular image and the first geometric boundary, a second geometric boundary of a second portion of the lumen of the vessel different from the first portion, the second portion of the lumen being located behind a guidewire disposed within the lumen;

determine, based on the first geometric boundary and the second geometric boundary, a third geometric boundary of the guidewire, the third geometric boundary being located within the first geometric boundary and the second geometric boundary;

measure, using the pressure measuring device disposed within the intravascular probe, one or more pressure values at one or more predetermined locations in the vessel;

determine based on the one or more pressure values, a first fractional flow reserve of the vessel;

iteratively correct a hyperemic microvascular resistance index until a predefined error limit is reached, wherein the hyperemic microvascular resistance index is determined using a calculated pressure drop value and the one or more pressure values, wherein the predefined error limit relates to the difference between the calculated pressure drop and the difference between the one or more pressure values;

calculate, based on the one or more pressure values and the corrected hyperemic microvascular resistance value, an estimated pressure drop associated with removal of the third geometric boundary from the vessel;

calculate, based on the estimated pressure drop, a first corrected fractional flow reserve; and display the first corrected fractional flow reserve.

15. The system of claim 14, wherein the second geometric boundary of the second portion of the lumen closes a perimeter of the lumen.

16. The system of claim 14, wherein the one or more processors are further configured to determine the first fractional flow reserve by dividing a first pressure measured distal to a stenosis by a second pressure measured in an ostium.

17. The system of claim 16, wherein the one or more processors are further configured to calculate the first corrected fractional flow reserve by correcting the first fractional flow reserve using three dimensional hydrodynamic equations, including the microvascular resistance index, and the first geometric boundary and the second geometric boundary.

18. The system of claim 14, wherein the one or more processors are further configured to:
determine a second fractional flow reserve in the vessel;
correct errors introduced by an obstruction in the vessel to determine a second corrected fractional flow reserve; and
compare the first corrected fractional flow reserve and the second corrected fractional flow reserve.

19. The system of claim 18, wherein the obstruction is the first intravascular probe, a second intravascular probe, a stenosis, a guidewire, or a stent.

20. The system of claim 18, wherein the one or more processors are further configured to output a damage index in response to the step of comparing.

* * * * *